US010368039B2

(12) United States Patent
Derenne et al.

(10) Patent No.: US 10,368,039 B2
(45) Date of Patent: *Jul. 30, 2019

(54) VIDEO MONITORING SYSTEM

(71) Applicant: Stryker Corporation, Kalamazoo, MI (US)

(72) Inventors: Richard A. Derenne, Portage, MI (US); Richard Thomas DeLuca, Kalamazoo, MI (US); Jason James Wroblewski, Kalamazoo, MI (US); Sanjay Dhall, Canton, MI (US); Xiyu Duan, Ann Arbor, MI (US); Vishal P. Lowalekar, Detroit, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/926,275

(22) Filed: Mar. 20, 2018

(65) Prior Publication Data
US 2018/0227547 A1 Aug. 9, 2018

Related U.S. Application Data

(63) Continuation of application No. 14/934,299, filed on Nov. 6, 2015, now abandoned, which is a
(Continued)

(51) Int. Cl.
H04N 7/18 (2006.01)
A61B 5/00 (2006.01)
(Continued)

(52) U.S. Cl.
CPC ............. H04N 7/185 (2013.01); A61B 5/002 (2013.01); A61B 5/0013 (2013.01); A61B 5/0033 (2013.01); A61B 5/112 (2013.01); A61B 5/1113 (2013.01); A61B 5/1128 (2013.01); A61B 5/7445 (2013.01); G01B 11/026 (2013.01);
(Continued)

(58) Field of Classification Search
None
See application file for complete search history.

(56) References Cited

U.S. PATENT DOCUMENTS 6,049,281 A * 4/2000 Osterweil ............ A61B 5/1128 340/573.1
9,295,390 B2 3/2016 Receveur et al.
(Continued)

Primary Examiner — Peter D Le
(74) Attorney, Agent, or Firm — Warner Norcross + Judd LLP

(57) ABSTRACT

An asset tracking system includes a camera adapted to capture images and output signals representative of the images. The camera may include one or more depth sensors that detect distances between the depth sensor and objects positioned within the field of view of the one or more cameras. A computer device processes the image signals and or depth signals from cameras and determines any one or more of the following: (a) whether a patient care protocol has been properly followed; (b) what condition a patient is in; (c) whether an infection control protocol has been properly followed; and (d) whether steps have been taken to reduce the risk of a patient from falling. Alerts may be issued if any conditions of importance are detected.

20 Claims, 16 Drawing Sheets

Related U.S. Application Data continuation of application No. 13/242,022, filed on Sep. 23, 2011, now Pat. No. 9,204,823.

(60) Provisional application No. 61/385,607, filed on Sep. 23, 2010.

(51) Int. Cl.

| | | |
|---|---|---|
| *A61B 5/11* | (2006.01) | |
| *G08B 21/04* | (2006.01) | |
| *G08B 21/24* | (2006.01) | |
| *G06F 19/00* | (2018.01) | |
| *G01B 11/02* | (2006.01) | |
| *H04N 5/33* | (2006.01) | |
| *G16H 40/20* | (2018.01) | |
| *G06K 9/00* | (2006.01) | |
| *G08B 21/22* | (2006.01) | |
| *G06Q 50/22* | (2018.01) | |

(52) U.S. Cl.
CPC ....... *G06F 19/3418* (2013.01); *G08B 21/043* (2013.01); *G08B 21/0476* (2013.01); *G08B 21/245* (2013.01); *G16H 40/20* (2018.01); *H04N 5/33* (2013.01); *A61B 5/1115* (2013.01); *A61B 5/1117* (2013.01); *A61B 5/1123* (2013.01); *A61B 5/6889* (2013.01); *A61B 5/6892* (2013.01); *A61B 5/7475* (2013.01); *A61B 2505/03* (2013.01); *G06K 9/00335* (2013.01); *G06K 9/00771* (2013.01); *G06Q 50/22* (2013.01); *G08B 21/22* (2013.01)

(56) References Cited

U.S. PATENT DOCUMENTS

| | | | |
|---|---|---|---|
| 9,569,591 B2 | 2/2017 | Vanderpohl, III | |
| 2002/0123687 A1* | 9/2002 | Birkenbach | A61B 5/0002 600/439 |
| 2006/0010601 A1* | 1/2006 | Riley | A47C 19/045 5/600 |
| 2006/0049936 A1* | 3/2006 | Collins, Jr. | A61B 5/1115 340/539.11 |
| 2007/0136102 A1* | 6/2007 | Rodgers | A61B 5/1113 705/3 |
| 2007/0174964 A1 | 8/2007 | Lemire et al. | |
| 2009/0070077 A1* | 3/2009 | Tian | G06T 7/593 703/1 |
| 2009/0119843 A1* | 5/2009 | Rodgers | A61B 5/1115 5/611 |
| 2009/0278934 A1* | 11/2009 | Ecker | G06K 9/00348 348/152 |
| 2011/0166891 A1* | 7/2011 | Zerhusen | A47B 23/046 705/3 |
| 2012/0025991 A1* | 2/2012 | O'Keefe | A61B 5/1115 340/573.4 |
| 2012/0154582 A1* | 6/2012 | Johnson | G06F 19/321 348/143 |
| 2016/0367420 A1 | 12/2016 | Zerhusen et al. | |

* cited by examiner

VIDEO MONITORING SYSTEM

CROSS-REFERENCE TO RELATED APPLICATION

This application is a continuation of U.S. patent application Ser. No. 14/934,299, filed Nov. 6, 2015 and entitled VIDEO MONITORING SYSTEM, which is a continuation of U.S. patent application Ser. No. 13/242,022 filed Sep. 23, 2011 and entitled VIDEO MONITORING SYSTEM, now U.S. Pat. No. 9,204,823 issued Dec. 8, 2015, which claims the benefit of U.S. provisional patent application Ser. No. 61/385,607, filed Sep. 23, 2010, by applicants Richard A. Derenne et al. and entitled VIDEO MONITORING SYSTEM, the complete disclosures of both of which are incorporated by reference herein in their entirety.

BACKGROUND

The present disclosure relates to systems and methods utilizing video cameras for monitoring patients, caregivers, equipment, and other items within a room in a caregiver setting, such as a hospital, nursing home, treatment center, or the like.

SUMMARY OF THE DISCLOSURE

According to various aspects of the systems and methods of the present disclosure, improved patient care is accomplished through the use of one or more video cameras positioned within a patient's room in order to provide patient care assistance in one or more of a variety of different manners. Such patient care assistance results from the analysis of video camera images that are used for any one or more of the following purposes: preventing patient falls, reducing the chances and/or spread of infection, ensuring patient care protocols are properly executed, and/or monitoring patient activity. Such analysis may take place remotely or in the room on one or more computer devices programmed to process and analyze video images.

According to one aspect, a video monitoring system is provided that includes at least one video camera and a computer device. The video camera captures video images and outputs signals representative of the video images to the computer device. The computer device processes the signals to determine at least one of the following items: (a) whether a patient care protocol has been properly followed; (b) what condition a patient is in; (c) whether an infection control protocol has been properly followed; and (d) whether steps have been taken to reduce the risk of a patient from falling.

In other aspects, the patient care protocol may include monitoring bed conditions and taking steps to reduce the risk of a patient falling include steps related to the bed. The computer device may determines whether a patient care protocol has been followed by first determining an identity of a clinician and the monitoring a sequence of steps performed by the clinician. The system may further be adapted to compare the sequence of steps to stored information indicative of specific tasks, and forward data regarding at least one of the specific tasks to another computer device if the sequence of steps matches the stored information. The specific tasks may include any one or more of turning a patient, dressing a wound, conducting a patient assessment, providing physical or respiratory therapy, starting a ventilator, and applying CPR. Another computer and/or software application may be in communication with the computer device and use the data regarding the specific tasks to make an entry in a patient's electronic medical record, or update a work flow computer system, or issue an alert to designated personnel.

In other embodiments, the computer device may determine from the output signals how long a patient has been lying on a particular side, front, or back of the patient's body. An alert may be issued to a caregiver if the patient has been lying on a particular side, front, or back of the patient for longer than a predetermined amount of time.

The system may also determine from the output signals a current angle of a head portion of a bed. An alert may be issued to one or more caregivers if the current angle of the head portion of the bed is less than a predetermined value.

The system may also determine from the output signals a type of bed positioned within a room, or the system may retrieve the type of bed within a given room from a database. Once the type of bed is known, the system may determine how low the bed is currently positioned in the room based on signals from the cameras, compare this height to a minimum height for that particular type of bed, and initiate an alert to a caregiver if the bed is not currently at its low position and a clinician is not in the room.

The system may determine from the camera signals if a patient is engaged in at least one of the following activities: eating, sleeping, exiting a bed, walking, walking to a bathroom, having a seizure, falling, getting entrapped in side rails on a bed, sitting in a chair, or exiting a chair. The system may also make an estimation of the likelihood of the patient attempting to leave a chair or bed based upon the movement and/or position of the patient, as well as other data. The estimation may be a numeric probability and may be communicated to caregivers. If the estimation exceeds a threshold, an alert may be issued.

The system may also monitor any one or more of the following: a clinician's hand washing and/or hand sterilization, one or more sterile fields, the usage of personal protection equipment; the movement of mobile objects for assessing cross infection potential, and cleaning. The monitoring of the clinician's hand washing may further include monitoring objects which are touched by a clinician after the clinician has washed his or her hands. The monitoring of sterile fields may include identifying what objects come into contact with a sterile object after the sterile object has been removed from its packaging, or monitoring objects that come into contact with an area that is intended to remain sterile, such as a wound area on a patient. The monitoring of the usage of personal protection equipment may include identifying if a clinician is wearing a gown, a mask, or gloves. The monitoring of mobile objects may include identifying objects within a room that are mobile, monitoring any such mobile objects are contacted by potential sources of infection, and issuing an alert to a clinician either prior to, or after, such a mobile object is moved out of the room. The monitoring of cleaning may include determining what areas of a room have not been cleaned and tracking items coming into contact with such non-cleaned areas. The monitoring of cleaning may also include determining if any non-typical areas of a room have been potentially contaminated.

The system may be used to reduce the likelihood of a patient fall by recognizing a behavior of a patient, recognizing a behavior or a clinician, determining whether fall protocols are in place, and/or assessing objective indicators of a patient's condition. The recognition of patient behavior may include using the recognized behavior to predict actions that may lead to a fall, such as getting out of a chair or bed. Such predictions may be based upon a patient movement of sheets, a patient clearance of one or more objects from his or her path, a patient leaning forward, a patient locating footwear, and/or a patient grasping an object for lifting support.

The recognition of patient behavior may also include identifying if a patient is using the arms of a chair or a rocking motion to get up, identifying a patient's stooped posture, identifying a patient's short steps, identifying a patient's grasping of nearby furniture, or performing Morse gait assessment of the patient.

The system may also be configured to recognize a patient fall after the patient has fallen. Such recognition may be based upon analyzing the camera output signals to determine a proximity of a patient's head to a floor, and/or any sudden movement of a patient's head or arms.

The system may analyze fall events and use data from an analyzed fall event to change a fall prevention algorithm in a manner that makes the fall prevention algorithm more robust.

The system may automatically pause a bed exit alarm when a clinician is detected within a room in which the patient bed is located.

The system may also perform one or more checks to determine if fall prevention protocols are being followed. These may include monitoring a height of a bed, whether brakes on a bed have been set, whether side rails on a bed are in an up position, whether a bed exit detector has been set, whether a patient is wearing hip protectors, whether a patient is wearing a special ID identifying a fall risk, whether a patient is wearing a helmet, whether a patient is wearing anti-slip socks, whether a floor mat is an obstruction, whether any obstacles or spills are in a patient's path to a bathroom, and whether items needed by a patient are within an arm's length of the patient.

The objective assessment of a patient to determine a potential fall risk for a patient may include determining whether a patient grasps an object when arising, assessing the patient's gait, assessing a patient's IV or Heparin lock, and/or performing a Hendrichs II assessment. If a fall or fall possibility is detected by the system, an alert may be issued.

One or more of the video cameras used in the system may include, in addition to the ability to record digital images, the ability to sense distances from the camera to the objects or individuals that are positioned in the camera's field of view. Such depth sensing ability may be based upon the projection of infrared light and the detection of reflections of that infrared light by sensors that are part of the system. The depth information may be used in combination with the image information to determine the three dimensional position and/or movement of individuals and/or objects within the viewing field of the camera. In addition to, or as a replacement of the video camera, a thermal imaging camera may also be used. Such a camera would have the advantage of detecting one or more human beings obstructed by objects in view of the camera. This is especially true for a patient lying under a bed sheet. Such a thermal image camera could use infrared sensing technology or other thermal imaging technology.

Facial recognition features may also be used in order to assist in identifying specific caregivers and/or specific patients. Such facial recognition features may utilize eigenface and/or haarcascade functions.

It will be recognized by those skilled in the art that the system described herein may perform any combination of the functions described herein. It will also be recognized that the system may, in at least some embodiments, monitor only a single one of the conditions described herein, while in other embodiments, multiple of the conditions may be monitored. Still further, other embodiments may monitor all of the conditions described herein and/or other conditions not mentioned herein.

Before the various embodiments disclose herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components

DETAILED DESCRIPTION OF THE EMBODIMENTS

Figure 1:
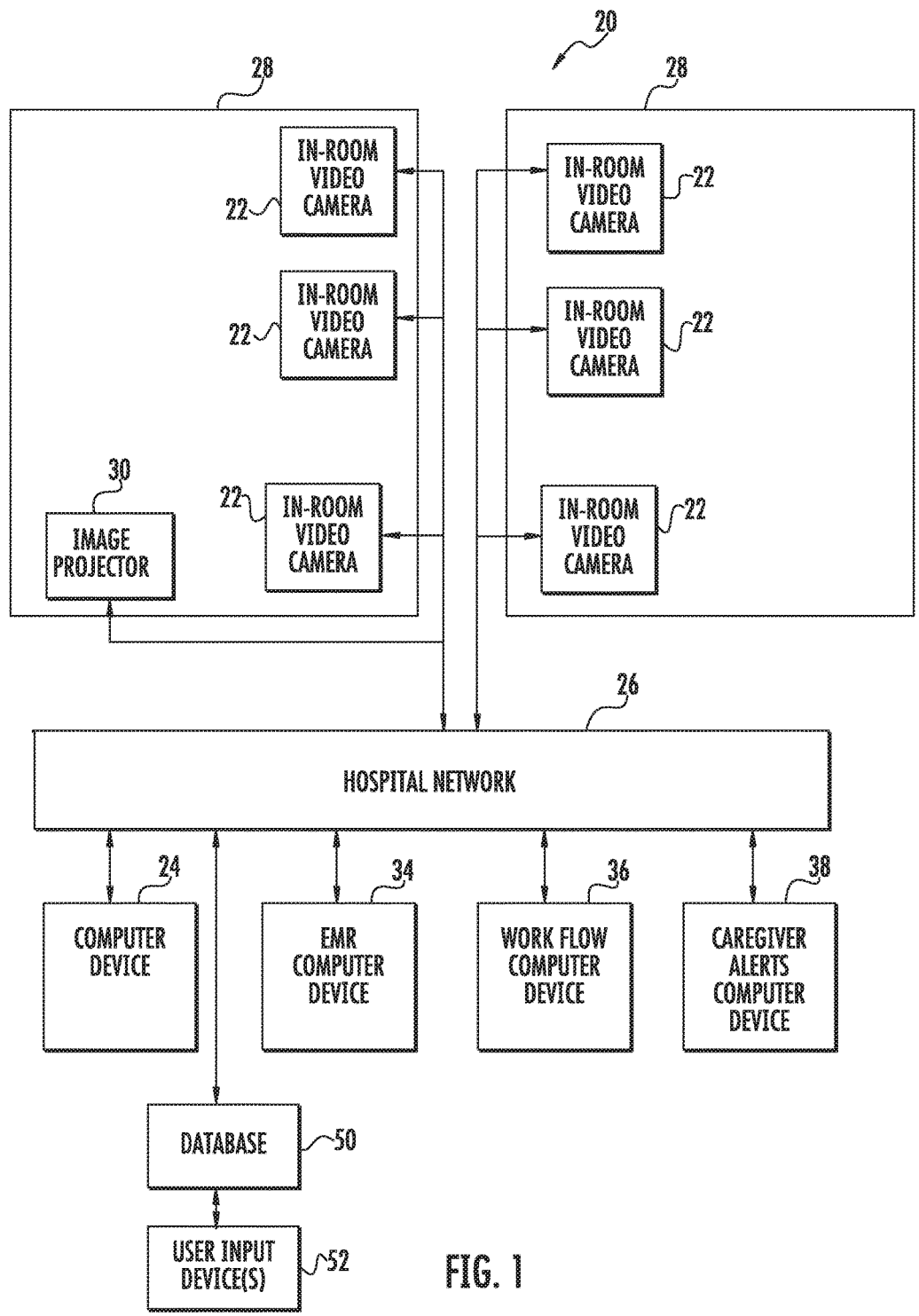
FIG. 1 is a block diagram of a video monitoring system according to a first embodiment.

A video monitoring system 20 according to a first embodiment is shown in FIG. 1. Monitoring system 20 includes one or more conventional video cameras 22 and/or other types of vision sensing or motion sensing equipment. Video monitoring system 20 is adapted to sense one or more conditions in a room or other environment, and/or to sense one or more actions undertaken by one or more persons in the room or other environment. The data gathered by the video monitoring system is processed by appropriate hardware and/or software to determine whether an alert or other type of notification should be forwarded to appropriate personnel. As was previously mentioned, video monitoring system 20 may be especially suited for use in a patient care environment, such as a hospital, nursing home, or other facility where patients are housed.

In some embodiments, video monitoring system 20 may be used to gather various information about the patient and the room in which the patient is located in order to alert appropriate personnel of any conditions that may increase the likelihood of the patient falling. Such information may include any one or more of the following types of information: (1) patient behavior and/or actions that may indicate that a patient is about to get out of a bed or chair; (2) clinician behavior and/or actions that detect when a clinician has entered or exited the patient's room; (3) the status of equipment settings, such as those associated with a bed or chair, which are useful in reducing the likelihood of a fall; and (4) assessments of a patient's gait that may indicate a greater potential for the patient falling. Still other types of information may be processed and/or used—either in lieu of, or in addition to, the foregoing information—in order to help prevent patient falls. Still further, video monitoring system 20 may also provide remote broadcasting of video information to remote locations, such as a nurse's station, a nurse's mobile device, a website accessible to relatives of the patient. Appropriate alarms or alerts may also be generated by system 20 and forwarded to the appropriate healthcare personnel when conditions or actions are detected that increase the potential of a patient fall.

In other embodiments, video monitoring system 20 may be used to gather information about the patient and the patient's room which is forwarded to appropriate personnel so that the risk of spreading infection either from or to the patient is reduced. In such embodiments, video monitoring system 20 may detect any one or more of the following conditions: (1) whether a clinician has washed his or her hands prior to approaching or touching a patient; (2) whether one or more sterile fields within the room are maintained and/or contaminated; (3) whether personal protection equipment is being used—such as masks, gowns, gloves, and the like—by personnel who enter the room; (4) whether objects within the room are mobile or stationary, and whether an alert should be issued to the appropriate personnel for proper cleaning of the object prior to its leaving and/or entering the room; and (5) whether areas within the room have been properly and/or completely cleaned. Upon the detection of any one or more of these conditions, system 20 may forward appropriate information regarding the condition to appropriate personnel in a manner that will be described in more detail below.

In other embodiments, video monitoring system 20 may be used to help ensure that patient care protocols are properly followed. For example, system 20 may automatically detect when a clinician enters the patient's room and monitor the activities performed by the clinician to ensure that one or more desired activities are performed. System 20 may also be used to monitor compliance with patient care protocols. Oftentimes, for example, such patient care protocols require that a patient be turned while positioned on the bed at certain intervals so as to lessen the likelihood of bed sores and/or other medical ailments. System 20 can be used to detect the absence or presence of such turning at the required intervals. System 20 may also be used to determine that the head of the patient's bed remains positioned at a desired angle, or that the height of the patient's bed remains at a desired level. Maintaining the angle of the head of the bed at a desired angle may be desirable in order to lessen the likelihood of ventilator associated pneumonia, and maintaining the bed at a low height may be desirable for reducing the likelihood of patient falls when getting into or out of the bed.

In still other embodiments, video monitoring system 20 may be used to monitor the patient within the room and alert the appropriate caregivers of any situations that they should be made aware of. These may include detecting whether the patient is in the room, has moved to the restroom, or has exited the room altogether. Other conditions may include determining if the patient is eating, sleeping, exiting the bed, walking, having a seizure, falling, getting entrapped in side rails, sitting in a recliner, or experiencing pain. Still other information about the patient may be gathered and processed.

In still other embodiments, any one or more of the foregoing uses of system 20 may be combined. That is, any one or more of the uses of fall prevention, infection control, patient care protocol compliance, or patient monitoring may be combined into a common video monitoring system 20. In still other embodiments, other uses are also possible, either alone or in combination with any one or more of these four uses. Such additional uses may include such things as asset tracking where system 20 recognizes the equipment and other assets positioned within the room and forwards that information to an asset tracking system so that the operators of the facility can determine where equipment is currently located within the facility. Still other uses are possible.

In one embodiment, any one or more of the video cameras 22 of system 20 may be a motion sensing device sold under the brand name Kinect™, or variations thereof, by Microsoft Corporation of Redmond, Wash., USA. The Kinect™ motion sensing device includes an RGB (red, green, blue) camera, a depth sensor, and a multi-array microphone. This device may be used to provide full-body 3D motion, facial recognition, and voice recognition capabilities. The depth sensor may include an infrared laser projector combined with a complementary metal oxide semiconductor (CMOS) sensor, which captures reflected signals from the laser projector and combines these signals with the RGB sensor signals. The Kinect™ motion sensing device may automatically detect the position of one or more persons and output data indicating the locations of multiple body portions, such as various joints of the person, multiple times a second. Such information may then be processed to determine any one or more of the conditions discussed herein.

In other embodiments, any one or more of the video cameras 22 may be a WAVI Xtion™ motion sensing system, or variations thereof, marketed by Asustek Computer, Inc., which has a principal place of business in Taipei, Taiwan. The WAVI Xtion™ motion sensing system uses one or more depth sensors to sense the position and movement of people without requiring the people to hold any objects.

In still other embodiments, other types of video cameras 22 may be used, or a combination of one or more of the Kinect™ cameras 22 may be used with one or more of the WAVI Xtion™ cameras 22. Still other combinations of cameras 22 may be used. Modifications may also be made to the camera 22, whether it includes a Kinect™ camera or a WAVI Xtion™ camera, or some other camera, in order to carry out the functions described herein, as would be known to one of ordinary skill in the art. It will further be understood that depth sensing devices may be used in system 20 that are physically separate from the image sensing portion of video cameras 22. The terms "video camera" or "camera," as used herein, will therefore encompass devices that only detect images, as well as devices that detect both images and depths. The images detected may refer to both ambient light images or thermal images, or still other types of images.

Whatever type or types of video cameras 22 that are used, such cameras 22 may include additional sensors beyond the image sensors and/or depth sensors, such as microphones, or other sensors. In some embodiments, it may be desirable to utilize more than one camera 22 within a room, or more than one camera 22 for a given patient. The use of multiple cameras for a given room or patient may decrease the likelihood of the camera's view being obstructed, and may increase the different types of information that may be gathered by the cameras 22. When multiple cameras 22 are used within a given room or for a given patient, the cameras 22 may all be of the same type, or they may consist of different types of cameras (e.g. some cameras may include both image sensors and depth detectors while others may only have image sensors).

The one or more cameras 22 that are positioned within a given room, or other location, are in electrical communication with a computer device 24 via a communications medium, such as, but not limited to, a hospital network 26, which may be a local area network (network), a wide area network (WAN), or any other type of network, including a network that is coupled to the Internet (FIG. 1). Network 26 may be an Ethernet-based network, or other type of network. The video cameras 22 are positioned within a patient care facility, such as a hospital, nursing home, or the like, and record images of various activity. Such images are converted to electrical signals which are forwarded to computer device 24 for processing in various manners, as will be described in more detail below. In the embodiment shown in FIG. 1, there are three video cameras 22 positioned within a single room 28. The number of video cameras 22 within a room, or other area, may be varied, and may depend upon what information is gathered from the video images. The physical location of the video cameras 22 within a room or other area may also vary in accordance with the layout of the room—such as, but not limited to, the physical location of the bed within the room, the location of the restroom, and the location of furniture or objects in the room—such that the cameras 22 are suitably positioned to be able to capture the desired images. As was noted previously, the video cameras 22 may include, in addition to an image sensor, a depth sensor (which may utilize infrared technology), or other sensors. The image sensor may be a digital image sensor in order to facilitate the digital processing of the recorded signals.

In some embodiments, one or more light projectors 30 may also be positioned within a room or other area of the patient care facility. The projector 30 may be a conventional projector that is capable of projecting images onto a screen, or onto other non-screen objects. The images that are projected by projector 30 are controlled by one or more computers, such as computer device 24. The images from the one or more projectors can show information to the patient or caregiver, such as: inventory levels of supplies, location of equipment or supplies, highlighting which objects are stable to use as a support during ambulation, highlighting objects that are sterile or not sterile, displaying a real-time pressure map on the patient's body, etc.

Computer device 24 may be a conventional server that communicates with both cameras 22 and projectors 30 over network 26, or it may be one or more personal computers (PCs), or it may be a dedicated electronic structure configured to carry out the logic and algorithms described herein, or any combination of these or other known devices capable of carrying out the logic and algorithms described herein. Such dedicated electronic structures may include any combination of one or more processors, systems on chip (SoC), field programmable gate arrays (FPGA), microcontrollers, discrete logic circuitry, software and/or firmware. Regardless of whether computer device 24 is a single physical device, or is multiple physical devices working together (which may be located in different physical locations), computer device 24 represents the hardware, software and/or firmware necessary to carry out the algorithms described herein.

In the embodiment shown in FIG. 1, the cameras 22 within each room 28 communicate their electronic images to computer device 24 over network 26. If cameras 22 include a depth sensor and/or microphones, the depth sensor signals and/or microphone signals are also forwarded to computer device 24 over network 26. The architecture of FIG. 1 may be modified in a variety of different manners.

Figure 2:
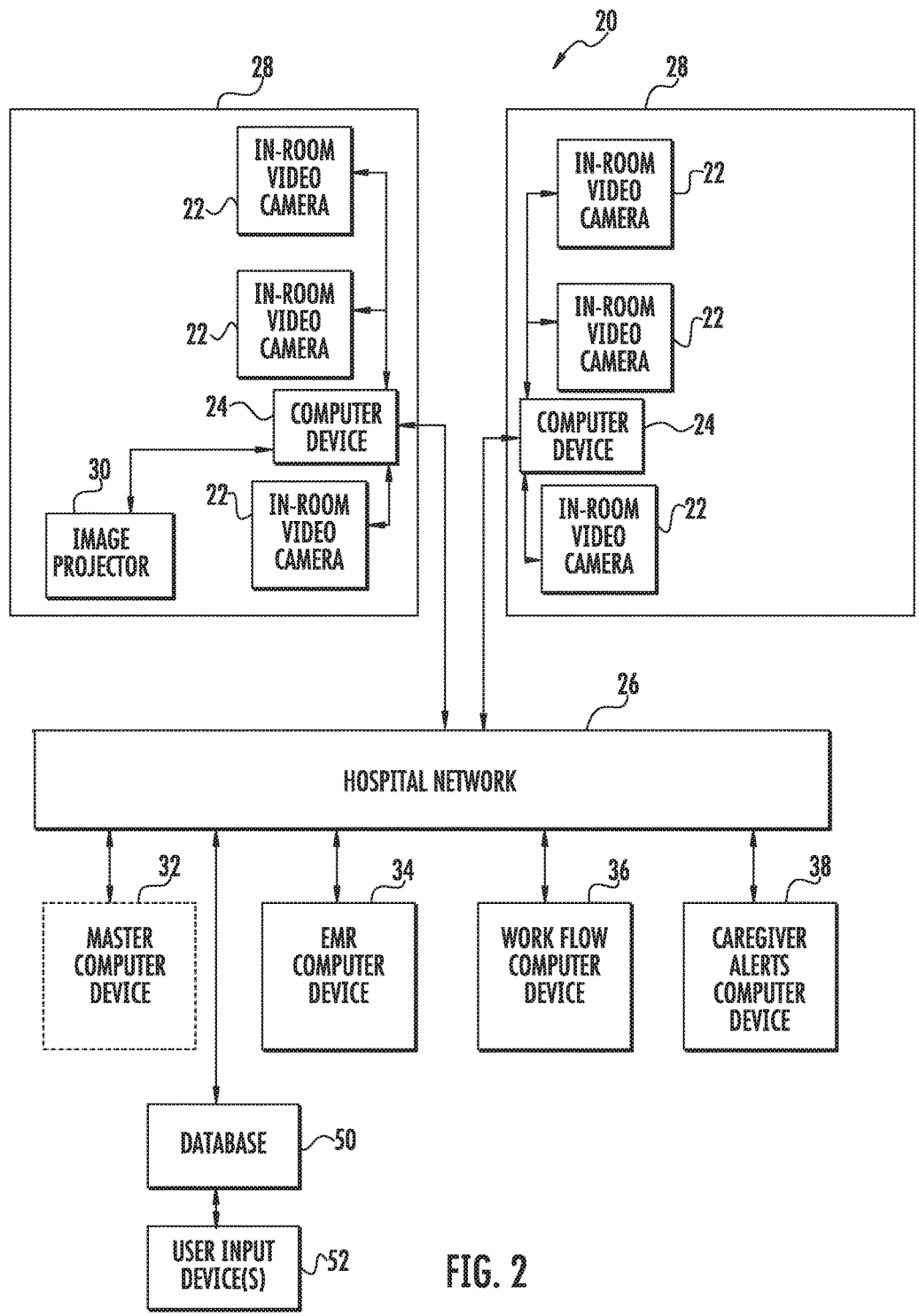
FIG. 2 is a block diagram of a video monitoring system according to a second embodiment.

One such variation is shown in FIG. 2, which illustrates a computer device 24 positioned in each room that is dedicated to processing the images and/or depth sensor readings generated by the cameras 22 positioned within that room. The in-room computer devices 24 in FIG. 2 may also be programmed to control the one or more image projectors 30. After processing all or a portion of the data received from the cameras 22, the in-room computer devices 24 may transmit messages regarding such processing onto the hospital network 26. Such messages may be sent to a master computer device 32 for further processing or, alternatively, such messages may be forwarded directly to one or more other computer devices that are in communication with network 26, such as, but not limited to, an electronic medical records (EMR) computer device 34, a work flow management computer device 36, a caregiver alerts computer device 38, an admissions, discharge, and transfer (ADT) computer device (not shown), or any other computer device in communication with network 26.

In an alternative embodiment (not shown), each video camera 22 may include its own computer device 24 or its own portion of computer device 24, either separately attached thereto, or integrated into the camera 22 itself. In such an embodiment, each computer device 24 is dedicated to processing, or pre-processing, the electronic images, depth sensor readings, and/or voice signals gathered by the associated video camera 22. The results of such processing, or pre-processing, may then be forwarded directly to network 26, or to one or more intermediate computers (not shown) before being sent to network 26. Computer devices 24 provide the software intelligence for processing the images, depth sensor data, and/or voice data recorded by cameras 22, and the precise physical location of this intelligence can vary in a wide variety of different manners, from embodiments in which all the intelligence is centrally located to other embodiments wherein multiple computing structures are included and the intelligence is physically distributed throughout the care giving facility.

Any of the computer devices in communication with network 26, such as EMR device 34, work flow device 36, caregiver alerts device 38, and the ADT device may comprise one or more conventional servers, PCs, software applications, or other known computing devices. EMR computer device 34 may be a conventional computer device of software application adapted to store and process patient electronic medical records. Information gathered from one or more video cameras 22 and processed by computer device 24 and/or master computer device 32 may therefore be transferred to EMR device 34 such that the processed information is automatically entered into a particular patient's EMR.

Work flow computer device 36 may be a conventional computer device or software application adapted to manage the assignment of caregivers to particular patients and to oversee the performance of specific caregiver functions. Information gathered from one or more video cameras 22 and processed by computer device 24 and/or master computer device 32 may therefore be transferred to work flow computer device 26, thereby avoiding the need for manual entry of such information. Such information may include data identifying the completion, or partial completion, of one or more caregiver tasks. Such information may also include data that indicates tasks, or partial tasks, that have yet to be competed.

Caregiver alerts computer device 38 may also be a conventional computer device or software application that is adapted to communicate alerts to caregivers. Computer device 38 may be part of a conventional nurse call computer system, may be completed integrated into such a nurse call computer system, or it may be a stand-alone system separate from the nurse call system. Regardless of its relationship to a nurse call system, caregiver alerts computer device 38 is adapted to forward alerts to caregivers when information about a patient warrants. Such alerts may be forwarded wirelessly to portable communication devices carried by the caregivers (e.g. pagers, personal digital assistants, tablet computers, laptop computers, Blackberries, cell phones, etc), or they may be forwarded to nurses stations or audio stations within the vicinity of one or more designated caregivers. Such alerts may be based upon a variety of different information, such as the fact that a patient is about to exit, or has exited, his or her bed, a patient is experiencing pain or discomfort, a patient has fallen, a patient's bed settings have changed, or a number of different events or status changes, many of which are discussed below in more detail.

As was noted above, the precise number and location of cameras 22 within a given room or other area may vary, depending upon the data that is intended to be captured by the cameras 22. In some embodiments, cameras 22 may be mounted to the walls, the ceiling, objects within a room, such as the hospital bed or other furniture, or in still other locations. Each camera 22 may be either mounted in a fixed orientation, or it may be coupled to a mounting structure that allows the orientation of the camera to be automatically adjusted by computer device 24 such that the camera may record images of different areas of the room by adjusting its orientation. Still further, each camera 22 may include zoom features that allow computer device 24, or another intelligent device, to control the zooming in and zooming out of the cameras 22 such that both close-up images and wider field of view images may be recorded, as desired.

Each computer device 24 includes software installed thereon that is adapted to process the sensor signals recorded by cameras 22. Such software may be conventional software, or include conventional software components, for recognizing video images and processing the information contained therein. In at least some embodiments, such software may combine commercially available software modules with customized software dedicated to carrying out the functions and algorithms described herein. As one example, such commercially available software may include OpenCV, which is an open source computer visions library supported by Willow Garage of Menlo Park, Calif. The OpenCV library has been released under the Berkeley Software Distribution (BSD) open source license. Customized software may be added to interact with, modify, and/or utilize one or more software components of the OpenCV library in order to carry out the algorithms described herein. Other commercially available software may also be used, either in addition to or in lieu of the OpenCV library.

In addition to the components described above, video monitoring system 20 may also include one or more databases 50 (FIGS. 1 and 2). Each database 50 is constructed to be accessible by computer device 24 such that computer device 24 may use the contents of database 50 in carrying out one or more of the algorithms described herein. In one embodiment, such as shown in FIG. 1, database 50 may be placed in communication with computer network 26 such that computer device 24 can access the contents of database 50 over network 26. In other embodiments, database 50 may be located elsewhere. One or more user input devices 52 may also be included in system 20 in order to add, update, or delete information contained with database 50. Such user input devices may include keyboards, cameras, scanners, touch screens, bar code readers, or other types of devices.

Database 50 may contain information that is useful for one or more of the algorithms carried out by system 20. This information may include photographic and/or other physical characteristic information of all of the current clinicians and/or staff of the patient care facility so that system 20 can compare this information to the signals detected by cameras 22 to identify if a person is a hospital employee and/or who the employee is. This information may also include photographic and/or other physical data of the current patients within the patient care facility so that patients can be recognized by system 20. The information within database 50 may also include data that is specific to individual rooms within the facility, such as the layout of the room, the location of restrooms, where and what objects are positioned within the room, the dimensions of the room, the location of room doors, the heights of floors, suitable or designated locations within the rooms for placing signs, and other useful information. The database may also include identifying information for identifying objects and assets, such as equipment used within the patient care facility. Such identifying information may include information about the shape, size, and/or colors of objects that system 20 is designed to detect. Still other information may be included within database 50. The data stored therein and the uses made of that data will be described in greater detail below.

Figure 13:
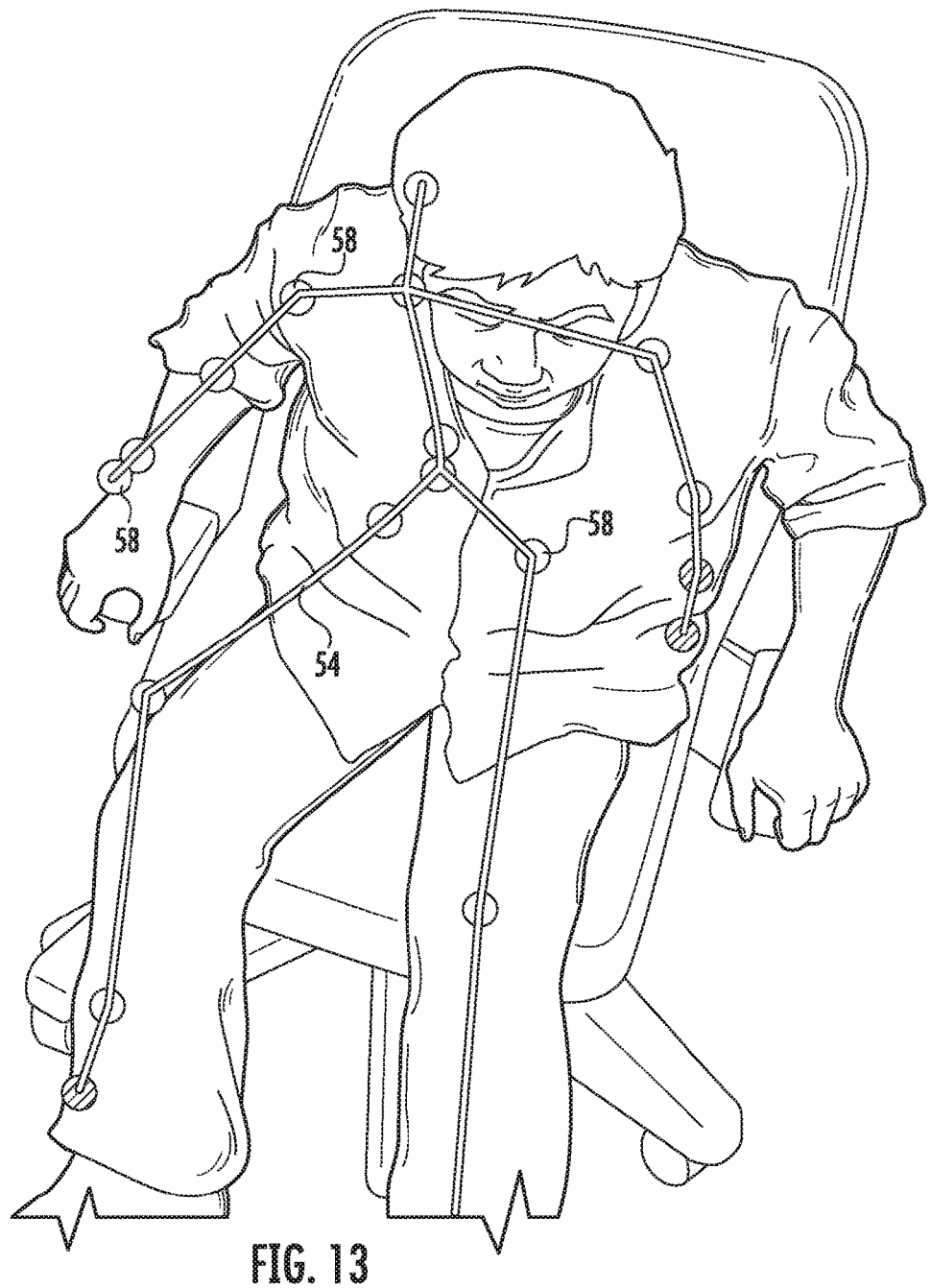
FIG. 13 is a perspective view of a patient seated in a chair shown with a computer-generated skeleton that corresponds to the patient's current position.

Video monitoring system 20 is configured to detect people who appear in the images detected by cameras 22. The detection of such people can be carried out in known manners, as would be known to one of ordinary skill in the art. In at least one embodiment, system 20 detects such people and generates a rudimentary skeleton 54 that corresponds to the current location of each individual detected by cameras 22. FIG. 13 shows one example of such a skeleton 54 superimposed upon an image of an individual 56 detected by one or more cameras 22. Skeleton 54 includes a plurality of points 58 whose three dimensional positions are computed by computer device 24, or any other suitable computational portion of system 20. In this embodiment, skeleton 54 includes points 58 that are intended to correspond to the individual's head, neck, shoulders, elbows, wrists, hands, trunk, hips, knees, ankles, and feet. In other embodiments, skeleton 54 may include fewer or less points 58 corresponding to other portions of a patient's body.

For each point 58 of skeleton 54, system 20 computes the three dimensional position of that point multiple times a second. The knowledge of the position of these points is used to determine various information about the patient, either alone or in combination with the knowledge of other points in the room, as will be discussed in greater detail below. For example, the angle of the patient's trunk (which may be defined as the angle of the line segment connecting a trunk point to a neck point, or in other manners) may be used in an algorithm to determine whether a patient in a chair is leaning toward a side of the chair, and therefore may be at greater risk of a fall. The position of the hands relative to each other and/or relative to the chair may also provide an indication of an intent by the patient to get up out of the chair. For example, placing both hands on the armrests may indicate that the patient is about to stand up. Alternatively, a patient who places both hands on the same armrest may also be an indication of an intent to get up out of the chair. Many other algorithms are described in greater detail below that use the position of body points 58 relative to objects in the room and relative to each other to determine conditions of interest.

Further, for any of the algorithms discussed below, a patient's head and face may be identified based on the skeleton so that a software algorithm can automatically blur the face to protect the patient's identity. In this manner, any images that are recorded and later played back will appear having a blurred-face patient, thereby protecting the patient's identify. Such blurring can even be used, if desired, in situations (described below) where system 20 identifies a patient by facial recognition. In such cases, system 20 may use the unblurred image data to determine the patient's identity through facial recognition, but only store blurred facial images so that any later playback will show a patient with an anonymous, blurred face. The identification of the patient through facial recognition may then be used for determining which medical records certain information should be forwarded to, or for other internal purposes. In this manner, the patient's identify can still be determined, but all visual records of the patient will not carry any visual images that identify the patient to viewers of the visual images.

In general, cameras 22 may be positioned to record image information useful for any one or more of the following purposes: ensuring proper patient care protocols are followed; identifying the type of behavior of a patient or the patient's condition; reducing the risk of infection and/or assisting in the containment of possible infectious agents; and/or taking measures to either reduce the likelihood of a patient falling, or to respond to a patient quickly after a fall has occurred. Further information about the use of cameras 22 and computer device 24 for effecting these purposes, as well as other purposes, is provided below.

A. Protocol Compliance

System 20 may be used to help ensure that patient care protocols used by a healthcare facility are followed. Depending upon the condition of the patient, different care protocols may be implemented in order to provide care that is optimally tailored to that patient. System 20 may be used in a variety of different manners for helping to ensure these protocols are properly followed. In some embodiments, system 20 may recognize behaviors of a clinician and forward information about that behavior to the appropriate hospital computer or server, such as EMR computer device 34, work flow computer device 36, caregiver alerting computer device 38, or some other computer device. System 20 may also look for fall risk signage amongst the visual images recorded by any of cameras 22 to determine if a patient is at risk for falling, as well as to monitor whether a patient's bed has been put into the proper configuration for that particular patient's medical condition. An alert may also be issued by system 20 if signage is not detected when such signage should be present for a particular patient or for a particular location.

1. Generic Clinician Behavior Recognition

Figure 3:
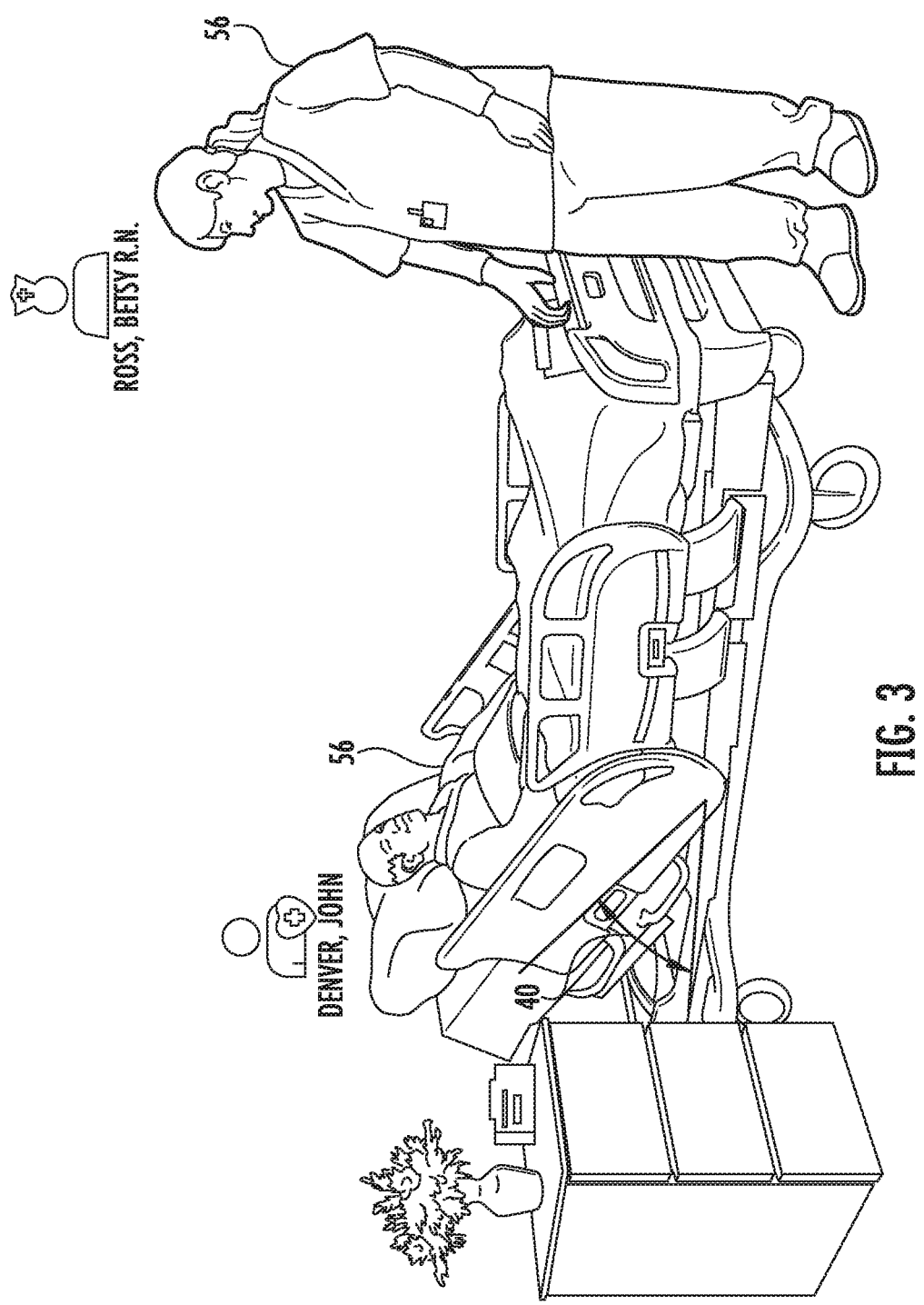
FIG. 3 is a perspective view of an illustrative patient care room, such as a hospital room, which may be detected by a video camera and analyzed in accordance with various principles of the disclosure discussed herein.

The images and depth readings recorded by cameras 22 may be processed to detect when a clinician enters a room. FIG. 3 shows an example of a specific clinician—arbitrarily designated as nurse Betsy Ross—within a patient room. System 20 may determine the identity of this specific caregiver by means of facial recognition software, a badge identification process based upon a specific badge that nurse Ross is carrying, by software that recognizes the attire she is wearing, by a combination of one or more of these means, or by other means.

Figure 14:
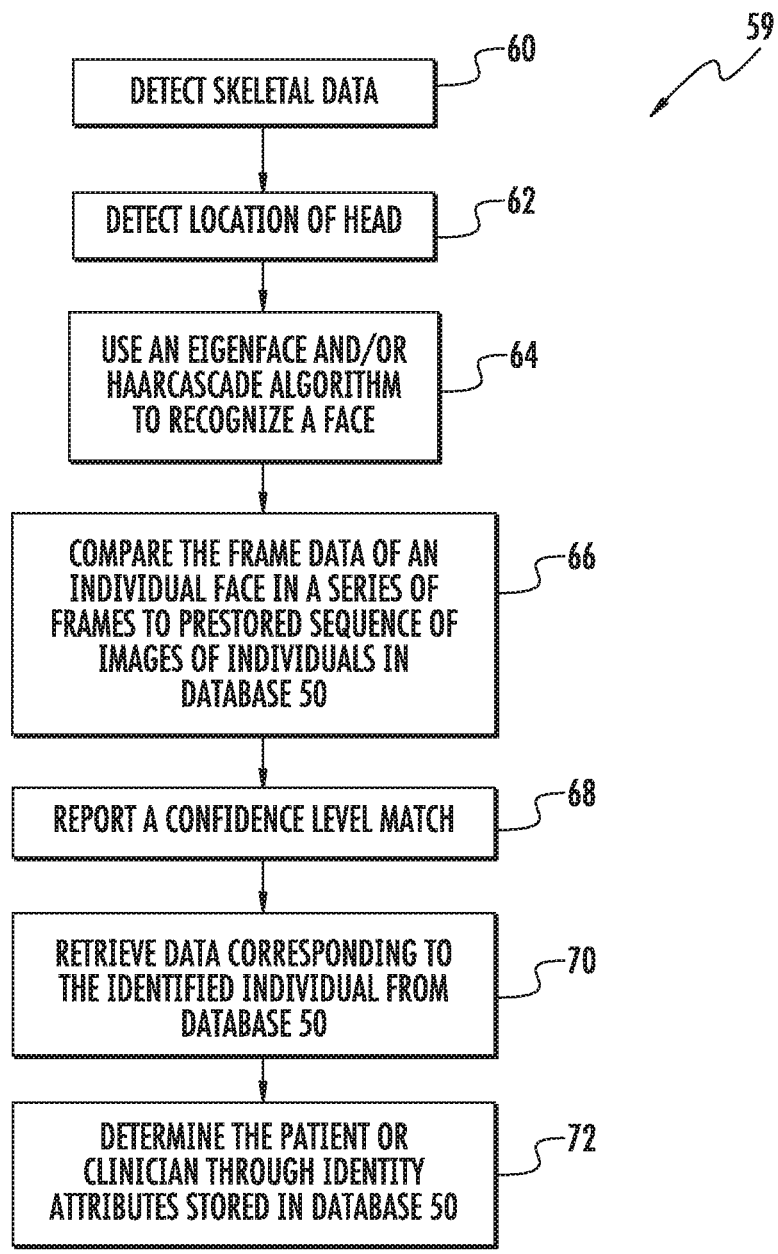
FIG. 14 is a diagram of one example of a face recognition algorithm that may be used by the video monitoring system.

One set of steps that may be followed by computer device 24, or any other computing device within system 20, to determine the identity of either a clinician or patient is a facial detection algorithm 59, which is illustrated in block format in FIG. 14. At step 60 of facial algorithm 59, system 20 detects the skeletal data corresponding to the individual or individuals 56 that are detected by cameras 22. This includes the locations of the points 58 in three dimensional space. At step 62, the detection of the skeletal data is used to identify the location of the head of the individual 56. After identifying the head of the individual, one or more specific facial recognition algorithms may be used at step 64 to determine the identity of the individual 56. In the algorithm 59 of FIG. 14, both an eigenface and haarcascade algorithm are identified as possible algorithms for identifying a person's face. Other algorithms may be used, either in lieu of, or in addition to, these algorithms.

The steps used by system 20 in recognizing a face at step 64 include the additional steps of selecting the best matching candidate from a database, such as database 50, of potential matches at step 66; reporting a confidence level for this match at step 68, retrieving data about the individual whose face is deemed a match (e.g. name, title, etc.); and identifying the individual on one or more screens that are in electrical communication with system 20 at step 72. After the individual 56 has been identified, the actions undertaken by that individual may be monitored by system 20 and recorded in a manner that correlates those actions to that particular individual. This will provide a record of the actions of those individuals so that proof of compliance, or non-compliance, will be available for authorized personnel having access to the data stored by system 20.

In addition to identifying who individuals are within a given room or other area, system 20 also records the data generated from cameras 22 that show the movement of the caregiver and/or patient. Any objects that are involved in this series of movements are also recorded and analyzed by computer device 24. The recorded and analyzed data is compared to a predetermined database of sequential behaviors which may include objects. When the recorded data closely resembles a stored object in the database, the movements are tagged as constituting a specific behavior or task. A time and/or date stamp may be added to this recorded data so that the time and/or date of the specific behavior or task is stored. When the behavior or task is a clinical protocol, information is sent to remote computer (such as EMR computer device 34) or it may be stored locally or displayed. Such local storage or display may occur within the room in which the task or behavior occurred, or it may occur at a nurse's workstation, at both locations, or at other locations. Computer device 24 may therefore include a display coupled thereto for displaying information, or computer device 24 may be in communication with one or more other computers that are capable of displaying information generated by computer device 24.

Clinical protocols that may be detected by system 20 include: turning a patient, dressing a wound, conducting an assessment of a patient, providing physical or respiratory therapy to a patient, starting a ventilator, and applying CPR, as well as any other known patient care protocols.

When system 20 determines that a clinician's behavior is a work flow item, information may be sent by computer device 24 to another remote computer (such as work flow computer device 36) or stored locally or displayed. Such work flow items may include determining when the following personnel enter or exit the room: x-ray technicians, doctor, cleaning staff, physical therapists, respiratory therapists, visitors, laboratory personnel, clergy, transfer team, or other personnel.

In carrying out any or all of the different uses described herein, system 20 may be configured such that cameras 22 are always recording data (such as visual images and depth information) and that the recorded data is buffered for some predetermined period of time. When an event is detected by the analysis of the data by computer device 24, or some other computer device, system 20 may transfer the data corresponding to the event to a longer term memory, or permanent memory such that a record is maintained of the images and other data corresponding to the event. For those recorded images and data in which no event is recorded, the buffered video images and data may be electronically discarded after some period of time such that the memory resources of the buffer may be reused for recording new images.

2. Turning Confirmation

When system 20 is used to monitor the turning of patients, system 20 may identify when a clinician is in the room. System 20 thereafter identifies—through the processing of data from one or more cameras 22—that the patient is turned and adds a date/time stamp to the data. System 20 then sends the data to remote computer. The remote computer may be an EMR computer, such as EMR computer device 34. Alternatively, or additionally, system 20 may store and/or displays the data locally. System 20 may further identify what side a patient is on (left, right, back, front) and track how long the patient has been on a particular side. System 20 may further send an alert to a clinician if patient has been on a particular side longer than a predetermined time. Such an alert may be forwarded to the clinician by sending a signal to caregiver alert computer device 38, which is programmed to carry out the alerting process.

3. HOB (Head of Bed) Angle Monitoring

System 20 may also be configured such that one or more cameras 22 are positioned to measure a Fowler angle 40 (FIG. 3), which is the angle the head section of the bed makes with respect to either horizontal or the base of the bed. System 20 may be in communication with one or more additional computers via network 26 such that it receives an indication if a particular patient is supposed to maintain his or her head of bed angle above a specific angle, such as thirty degrees. Computer device 24 processes the images from cameras 22 to determine the head angle of the bed and, if a patient's HOB angle needs to be above 30 degrees, system 20 may send an alert if the HOB angle is lower than this. As with all alerts discussed herein, the alert may include a message sent from computer device 24 to network 26 which is picked up by caregiver alerts computer device 38 for forwarding to the appropriate personnel, or it may be any other type of alert. Such alerts may be useful in helping to prevent ventilator associated pneumonia.

In addition to monitoring the angle of the head of the bed on which the patient is positioned, system 20 may also monitor the angle of the patient's trunk, shoulder blades, and/or hips relative to the bed. These angles may desirably be measured if there is a chance that the patient is slouching, or otherwise not positioned at an angle in which the patient's trunk is generally aligned with the head of the bed, and therefore the patient's trunk angle does not match the head of bed angle. In such cases, it may be desirable for an alert to be issued such that a caregiver may reposition the patient in a manner in which his or her trunk is elevated so that the chances for ventilator associated pneumonia are reduced.

4. Height of Bed Monitoring

System 20 may also be configured such that one or more cameras 22 are positioned to measure a height H (FIG. 3) of the patient's bed. System 20 may identify the particular type of bed the patient is resting on by detecting a number of attributes of the bed via cameras 22 and then comparing these attributes to known attributes of specific types of beds. The known attributes may be stored in database 50, or elsewhere. The list of attributes may include dimensions for the detected bed, markings on the bed, structural features of the beds, identifiers positioned on the bed, or other information about the bed that can be used to distinguish the bed from other types of beds that may be present in the health care facility. If only one type of bed is used within the facility, then such comparisons may be omitted.

After a bed is detected by system 20, system 20 determines how high the bed is currently positioned (distance H in FIG. 3) above the ground. This number is then compared with the known minimum height for that particular bed. Such known heights may be stored in database 50. Indeed, database 50 may contain values of the minimum heights for each type of bed that may be present in the health care facility. System 20 may then send an alert if it detects that height H is greater than the known lowest height for that particular bed. In issuing this alert, a tolerance may be included to account for any measurement errors by system 20 so that bed height alerts are not issued in response to inaccurate height measurements by system 20. Sending such alerts may help in preventing patient falls, and/or in minimizing any negative consequences from any falls that might occur.

In some embodiments, system 20 may be configured to only send a low bed height alert if the bed isn't at its lowest height and a clinician is not in the room. Thus, alerts will not be sent if a clinician is present and adjustments to the bed height are made. If the clinician exits the room with the bed not returned to its lowest height, however, system 20 may issue an alert to remind a caregiver to return the bed to its lowest height.

B. Patient Activity Identification

System 20 may further be used to identify activities or conditions of a patient. Such activities or conditions may generate information that can be used to issue alerts, or for other purposes.

As was described above, system 20 may identify the individuals who are in a room, including both clinicians and the patient, using a facial recognition algorithm, such as algorithm 59 (FIG. 14). Either in addition to, or in lieu of, facial recognition algorithm 59, system 20 may identify a specific patient through wrist band identification, attire recognition, location on a patient bed, a combination of these, or through other features. Once a patient is identified, system 20 may monitor the patient for a wide variety of different activities and/or conditions.

Figure 4:
FIG. 4 is a perspective view of a patient eating that may be captured by one or more video cameras.
Figure 6:
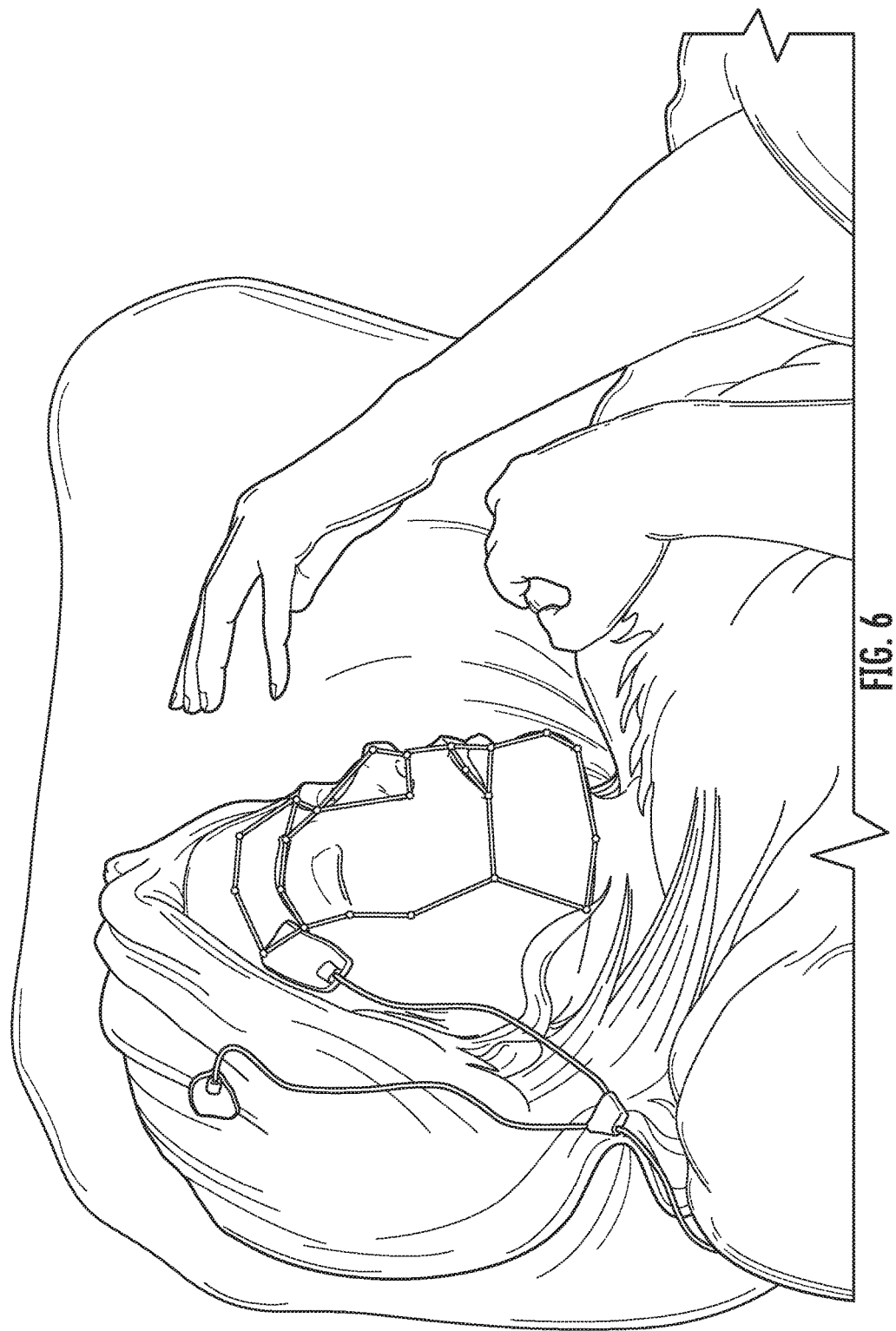
FIG. 6 is a perspective view of a patient asleep that may be captured by one or more video cameras.
Figure 7:
FIG. 7 is a perspective view of a patient experiencing pain that may be captured by one or more video cameras.

System 20 may record a series of sequential movements made by the patient. Object recognition data may further be added to the sequential movement data such that any objects that the patient interacts with are identified. The recorded data is analyzed and compared to a predetermined database of sequential behaviors and/or objects. When the recorded data closely resembles one in the database, the movements are tagged as a certain behavior. A time/date stamp may added to this data. The recorded patient behaviors may include any one or more of the following: eating (FIG. 4), exiting the bed, walking, walking to the bathroom, having a seizure, falling, getting entrapped in side rails (FIG. 5), sleeping (FIG. 6), experiencing pain (FIG. 7), sitting in a recliner, etc. System 20 may then send this information to a remote computer, to a display, or as an alert to a caregiver.

Figure 5:
FIG. 5 is a perspective view of a patient entrapped against a side rail of a bed that may be captured by one or more video cameras.
Figure 15:
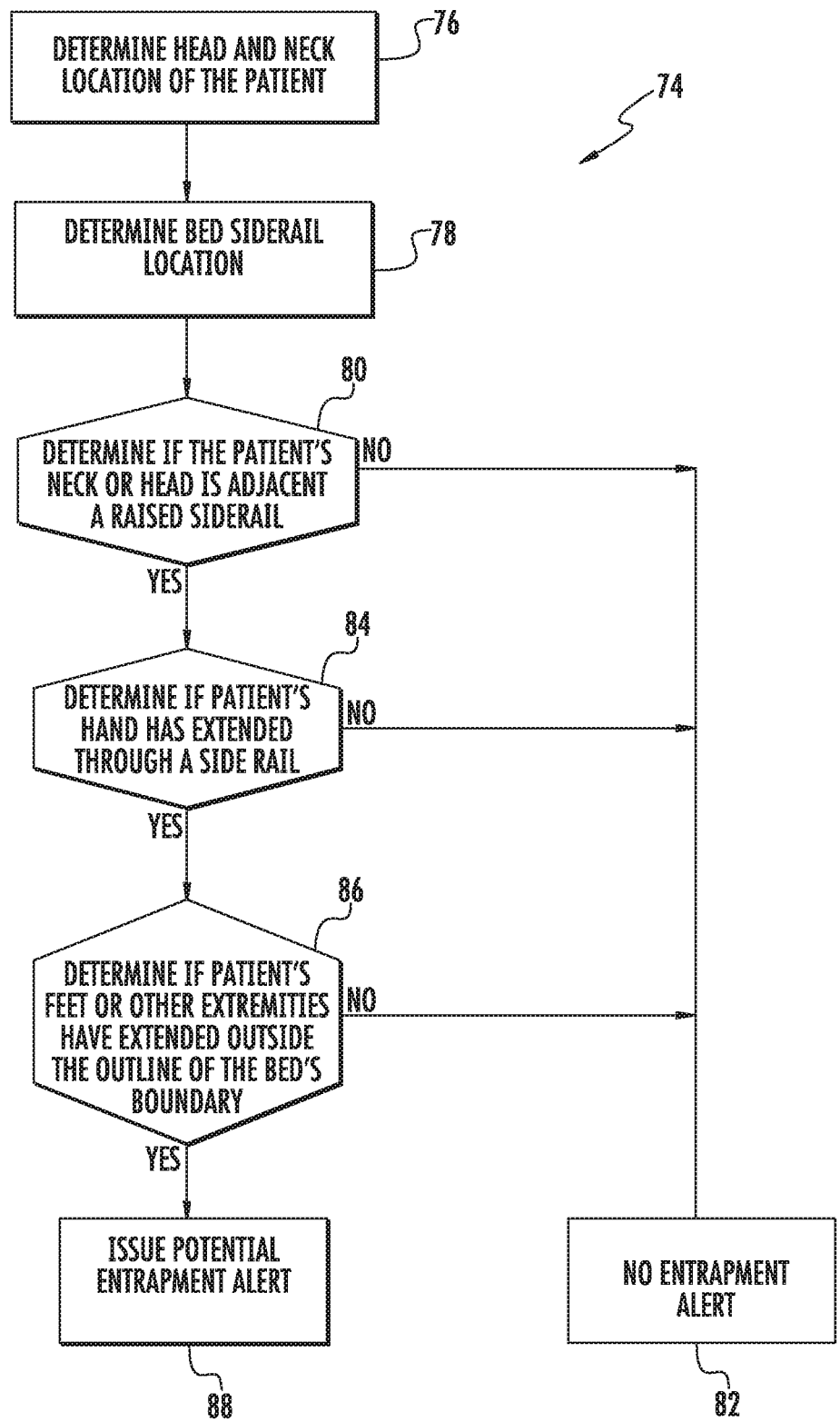
FIG. 15 is a diagram of one example of a patient entrapment algorithm that may be used by the video monitoring system.

FIG. 15 illustrates one example of a patient entrapment determination algorithm 74. This algorithm determines if an alert should be issued indicating that a patient may have become entrapped between a siderail of the bed and the mattress or other surface of the bed. FIG. 5 illustrates one example of a patient that is entrapped in such a manner. Algorithm 74 starts at step 76, in which system 20—either via computer device 24 or another computing device—determines the head and neck locations of the patient from the skeletal data generated from cameras 22. At step 78, computer device 24 determines the location of the siderails and whether the siderails are in the up or down position. If they are in the down position, then no entrapment alert will be issued. If they are in the up position, then computer device 24 proceeds to step 80. At step 80, computer device 24 determines the patient's head or neck is adjacent to one of the up siderails. If not, computer device 24 moves to step 82 and does not issue any potential entrapment alert. If so, then computer device 24 moves to step 84 where it determines if the patient's hand or fingers have extended through the siderail. If so, control proceeds to step 86. If not, control moves to step 82 and no alert is issued. At step 86, computer device 24 determines if any other extremity of the patient has moved beyond the boundaries of the bed. If so, then a potential entrapment alert is issued at step 88. If not, no alert is issued.

It will be understood by those skilled in the art that algorithm 74 may be modified in many ways for determining if an entrapment alert should or should not be issued. As one example, an alert may be issued if fewer than all of the conditions determined in steps 80, 84, and 86 are present. Alternatively, still other conditions may be factored into the algorithm, or substituted for the steps illustrated in FIG. 15.

System 20 may also be configured to detect if a patient is eating, as was previously mentioned. A variety of different algorithms may be used to detect such eating. As one example, an eating detection algorithm may first involve determining the location of the patient's head from the skeletal data. Thereafter, the location of the patient's lips and face may be detected in a series of frames captured by cameras 22. For one or more of the frames, the distance between the upper and lower lips may be calculated. Variations in this distance over a series of frames may be used as an indication that the patient is currently eating. These variations may also, or alternatively, be compared to baseline data stored in database 50 of the distance between the lips of the individual when images of him or her were previously captured during a known eating event.

An eating detection algorithm may also take into account, either in lieu of or in addition to the distance between the upper and lower lips, object detection information. Such object detection information may include the detection of a food tray positioned in the front of the patient. Other data that may be used also includes the movement of the patient's arms with respect to the patient's mouth and/or a food tray. Still other data may be used to detect if/when a patient eats.

With respect to determining when a patient is asleep, it is again possible for multiple different algorithms to be used in system 20. As one example, a sleep detection algorithm may first locate both eyes on the face and detect these positions for a series of frames captured by camera(s) 22. Once the position of the eyes are determined, system 20 may determine the location of the retinas within the patient's eyes. If the retinas are not visible for a predetermined amount of time and patient movement is substantially absent, the algorithm may determine that the patient is asleep. This information may stored for later retrieval by clinicians, or an alert may be issued if there is a desire for immediate notification of the patient falling asleep. The sleep detection algorithm can be modified in an opposite manner to detect if a patient is awake, if desired, and this information may also be stored for later retrieval or transmitted immediately for timely notification to selected personnel.

A patient pain detection algorithm may also be included within system 20. Such an algorithm may first include a step of identifying a patient within a room. After the patient is identified, comparisons of real time images of the patient with a baseline image may be performed at intervals. The baseline image may be stored in database 50, and may be derived from previous images taken while the patient is in the room, or an admissions photograph, or other sources. Such comparisons may focus on specific features of the patient's face, such as the distance between the patient's upper and lower lips, the distance between the patient's retina and his or her eyebrows (to detect eyebrow furrowing), and/or sound data detected by cameras 22 that indicates moaning, groaning, or other aural indicia of pain. If a threshold change in any one or more of these measured factors is met, a pain indication alert may be generated by system 20.

In addition to potential entrapment, eating, sleeping, and pain recognition, another patient behavior that system 20 may record and analyze is hand or arm gestures to signal a command for the caregiver or a device in the room. For example, raising a hand for more than five seconds may initiate a nurse call. Or, when combined with a projected user interface image onto a nearby surface (which may comprise projected images of buttons, or other user interface controls, and which may be projected by one or more projectors 30), hand motions that substantially simulate button pressing may control motions of the bed or other devices. In other words, one or more projectors 30 may project light images of a user interface onto a selected surface. When the patient moves his or her arms, fingers, or legs in a predefined manner relative to those images, such actions may be interpreted as the patient desiring a certain outcome.

Figure 16:
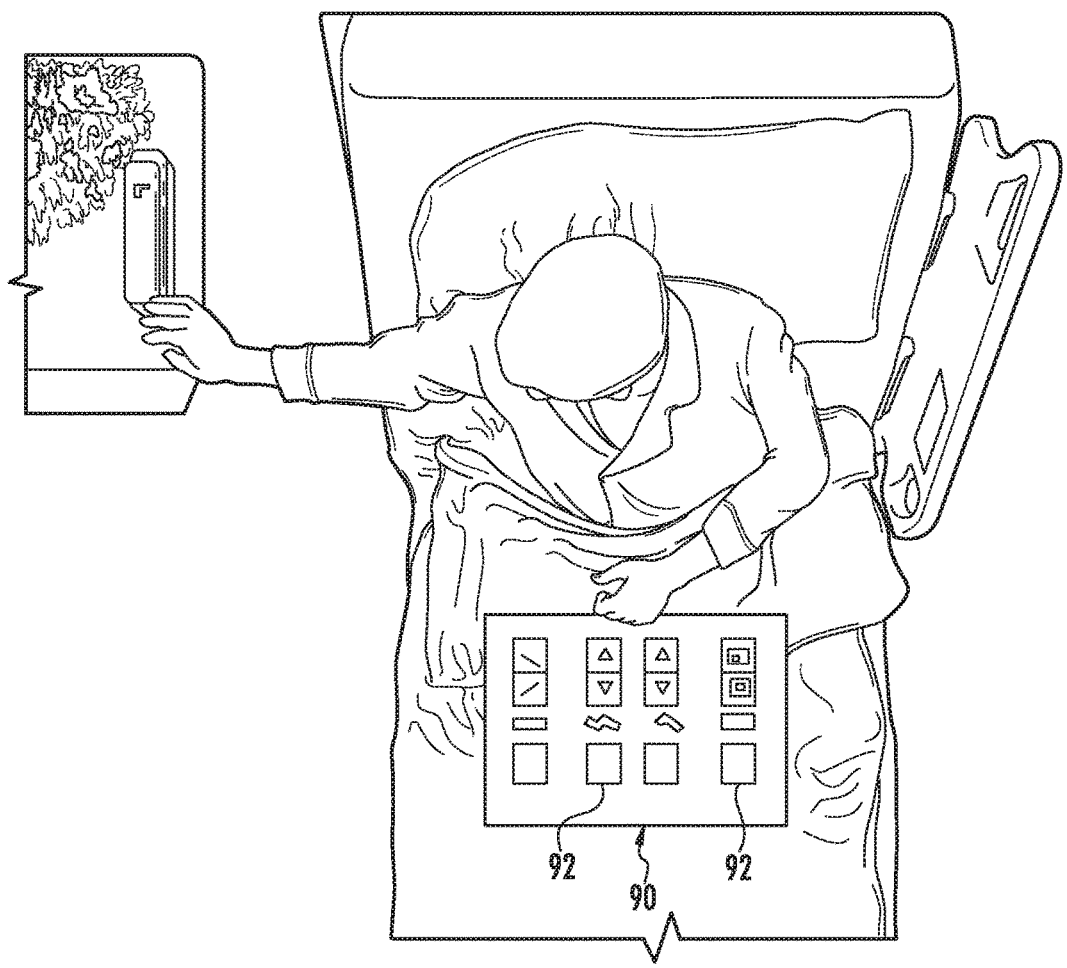
FIG. 16 is a perspective view of a projected image of a patient control menu projected onto an area of a bed in front of a patient.

An example of a light projected user interface 90 is shown in FIG. 16. User interface 90 includes multiple button images 92 that are displayed in front of the patient by image projector 30. The movement of the patient's hand or finger on top a selected one of these button images 92 may be interpreted as the patient desiring to press a real button corresponding to that button's image. System 20 may then act accordingly to cause the proper response. Images of such user interfaces may be projected for controlling the environment of the room (lights, TV, sound, radio, etc), adjustments to the bed, and/or for communicating with a nurse. System 20 may be configured to be in electrical communication with all of these devices such that, when a patient moves in a manner indicating a selection of a particular function (based on choosing control from a projected images of controls), system 20 causes the device to react in the manner desired by the patient.

C. Infection Control

System 20 may be used to help ensure that the risks for infection are reduced and/or to help contain infectious risks. System 20 may be used in a variety of different manners for helping to effectuate this purpose. In some embodiments, system 20 may recognize and monitor whether clinicians are washing their hands, whether sterile fields are maintained or potentially contaminated, whether personal protection equipment is being worn and/or used, whether there is a risk of cross infection, and/or whether cleaning has been completed, as well as assessing the quality of the cleaning process.

1. Hand Washing

Figure 8:
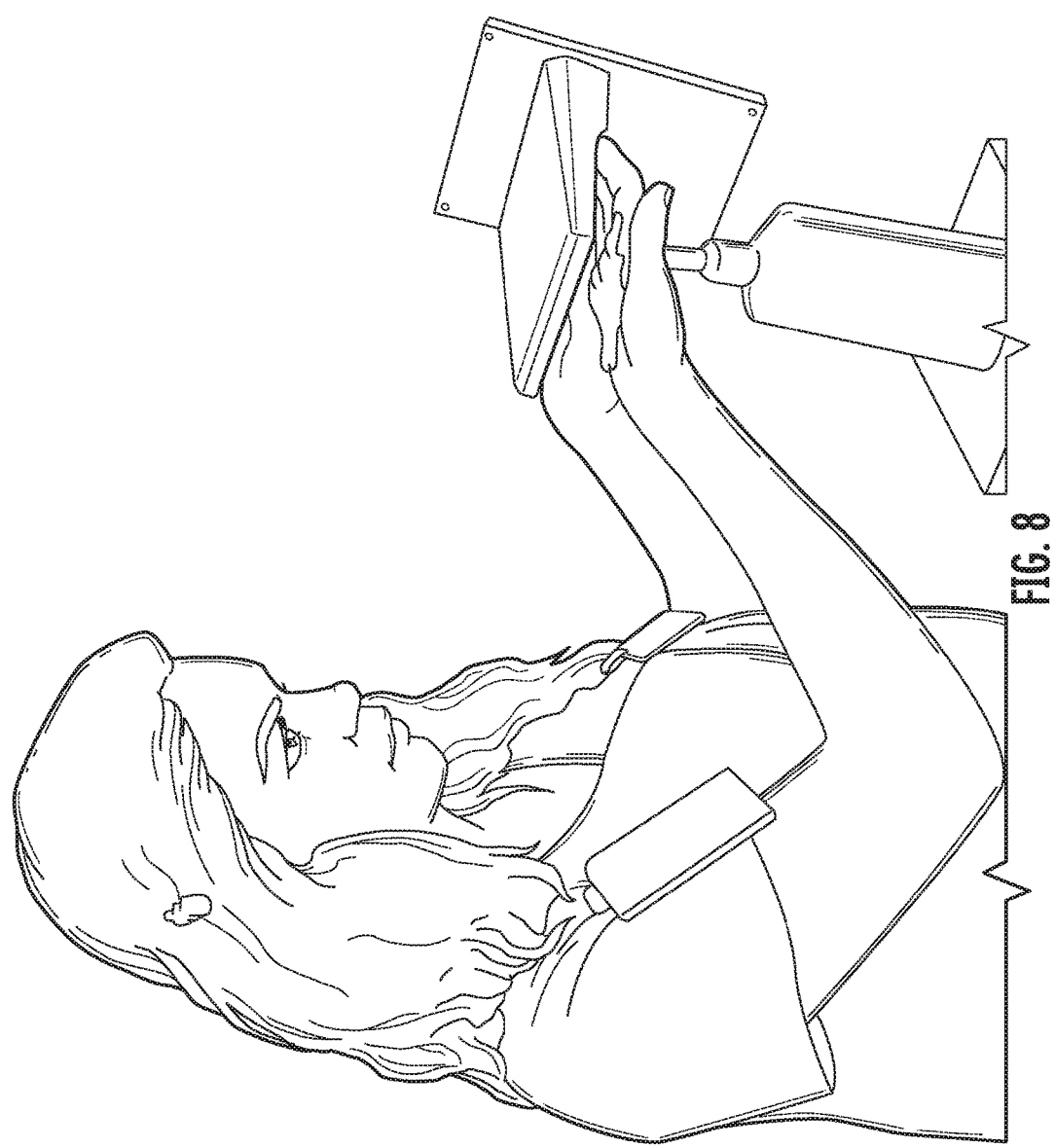
FIG. 8 is a perspective view of a clinician in the process of sanitizing her hands that may be captured by one or more video cameras.

System 20 may be adapted to monitor if a clinician washes his or her hands prior to approaching a patient. Such monitoring is accomplished through the use of one or more video cameras aimed at a sink, or other hand washing or sanitization station. FIG. 8 provides an example of an image that may be recorded by a camera 22 capturing a caregiver cleaning her hands. Images such as this, which may include depth data, are processed by computer device 24 to determine if a clinician has washed his or her hands prior to working with a patient. If system 20 detects that proper hand washing did not take place, the system may send a local alert to remind the clinician. System 20 may also track compliance with hand washing procedures.

In one embodiment, system 20 may determine if a clinician has washed his or her hands by first defining in 3D space an area within the room in which the sink, or other hand-washing instruments, are located. This information may be predetermined and retrieved from database 50 by system 20. After system 20 knows where the hand washing space is located, the system identifies individuals who enter the room and determines if they are clinicians or not, such as by using facial recognition algorithm 59, or by other means. If the person is a clinician, then a hand washing check is triggered. The location of the clinicians hands are monitored relative to the 3D space in which the cleaning instrument, such as a sink, is located. Multiple frames are recorded of the clinician's hands within this space and the time within this space is also recorded. If the amount of time within this space exceeds a preset time, then the hands may be considered to have been cleaned. A "hands washed" indication may appear on a screen viewable by health care personnel. The satisfactory washing of the hands may also be stored, including the underlying data, for later retrieval by authorized personnel. If the clinician's hands are not washed prior to the clinician touching an object in the room, an alert may be issued.

Figure 9:
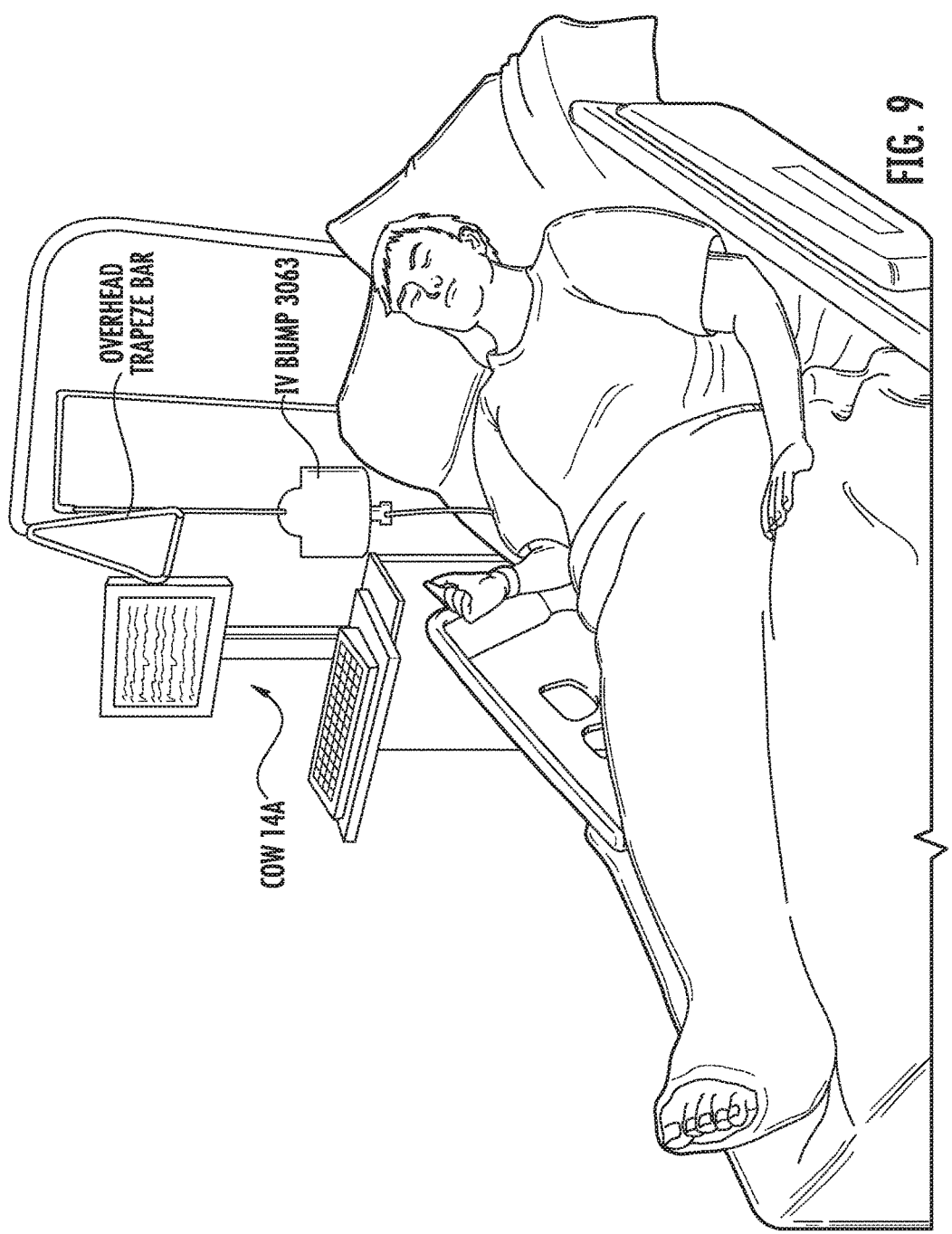
FIG. 9 is a perspective view of a patient in a bed, along with various associated medical equipment, that may be captured by one or more video cameras.

Cameras 22 may further be used to monitor potential contamination of hands after being washed. This may include recording which objects are touched by a caregiver that are potentially contaminated. Alerts may be issued in appropriate circumstances. The recording of what objects are touched in a room may include monitoring any and all objects that are positioned within a room. FIG. 9 illustrates an illustrative example of an image that may be taken by one or more cameras 22 that shows several objects whose contact with a clinician's hands, or with other objects, may be recorded. Such objects include an IV pump, an overhead trapeze bar, a personal computer, etc.

2. Sterile Field

System 20 may also process images and data from cameras 22 to identify objects in package as being sterile. System 20 may further identify when sterile objects are removed from packaging and monitor what touches the sterile objects once they are removed from the packaging. A local alert may be issued to warn the clinician of potential contamination if it is detected by system 20.

System 20 may also identify the location of a patient's dressing or open wound and monitor it such that only sterile objects approach this area. A local alert to warn the clinician of potential contamination may also be issued. As with all local alerts discussed herein, the local alert may be visual, audio, or a combination of these. Such alerts may be issued from a display within the room, or from other suitable means.

3. Personal Protection Equipment (PPE) Usage (Gowns, Gloves, Mask, Etc.)

System 20 may identify types of patients with appropriate isolation precautions, such as contact, airborne, etc. In such cases, system 20 may detect what kind of personal protection equipment (PPE) the clinician uses. Local alerts may be issued to remind the clinician if the cameras 22 and computer device 24 detect that proper PPE isn't used. System 20 may also track compliance with PPE usage. The touching of objects that are potentially contaminated may also be recorded by system 20. Local alerts to remind a clinician may be issued if proper PPE isn't used.

The detection of glove usage may be accomplished by first determining the location of the clinician's hands based upon the skeletal data gathered from cameras 22. After this location is determined, raster images of the clinician's hand regions may be gathered via cameras 22. The red, green, and blue (rgb) color values of these raster images may then be analyzed. If the color ranges are within a defined zone of colors corresponding to the colors that are expected for gloves, then the clinician's hands are considered to be gloved. If the colors fall outside the zone, then they are considered ungloved, and an alert may be issued.

The detection of gown usage may be accomplished in a somewhat similar manner. From the skeletal data gathered by cameras 22, the location of the clinician's shoulder points or hip joints may be determined in three dimensions. A region around these points or joints may be defined and a raster image of these regions may be gathered. Determining whether a gown is being worn may be accomplished by at least one of two different steps, or a combination of the two. In a first step, the rgb colors of the raster images are compared to a defined range of colors that correspond to the expected colors of a gown. If the detected colors fall within this range, the clinician is considered to be wearing a gown. If the detected colors fall outside this range, the clinician is considered to not be wearing a gown. In a second step, the rgb colors of a first region of the raster images may be compared to the rgb colors of another region of the raster images. The two regions may be located at spaced locations, such as one near the clinician's trunk, and another beneath the clinician's waistline. If the two regions of color are substantially the same, then the clinician may be considered to be wearing a gown.

4. Cross Infection from Mobile Objects

System 20 may identify what objects stay in the room ("stationary objects") versus those objects that leave the room ("mobile objects"), and further monitor potential infection of the "mobile" objects. A local alert may be issued to remind a clinician prior to a "mobile object" leaving the room that the mobile object may be contaminated. Such monitoring may be done in conjunction with the monitoring of cleaning (discussed below) such that mobile objects that have been cleaned are permitted to leave the room without generating an alert. The identification of such objects, as with the identification of any of the objects discussed herein, may be accomplished by comparing the detected shape, size, and other attributes of the object with the attributes of known objects stored in database 50. Alternatively, or in addition, object identification may be accomplished by detecting identifiers positioned on the object, such as badges, bar codes, or other types of detectable indicia.

5. Cleaning

System 20 may tracks what areas of the room have been cleaned. Such tracking may include recording what areas of a floor or other surface have been brushed by a broom, mop, cloth, or other cleaning utensil. If areas are missed, a local alert may be issued. Additionally, or alternatively, system 20 may utilize one or more projectors 30 to project a specific type of light onto the specific area of the surface that has not been cleaned. The light is displayed only on the area of the surface that has not been cleaned. The area illuminated by the light may be altered in substantially real time to match the cleaning being performed. In this manner, any remaining areas that are covered with projected light after the individual finishes cleaning will be highlighted as having been missed, and appropriate corrective cleaning can take place (at which point the projection of light onto those area will terminate).

As another alternative, system 20 may be configured in an opposite manner to shine a specific light upon all areas of a surface that have been cleaned. As the cleaner moves the cleaning utensil over the surface, system 20 alters the lighting projected by projector 30 such that the areas that have been cleaned have the specific light projected upon them. Thus, as the person cleans the surface, the areas covered by the specific projected light will keep getting larger and larger. If any spots are missed, the specific projected light will highlight these by the absence of light on those areas. The specific projected light therefore provides a visual cue to the cleaner of where he or she has yet to clean and where he or she has already cleaned.

Figure 10:
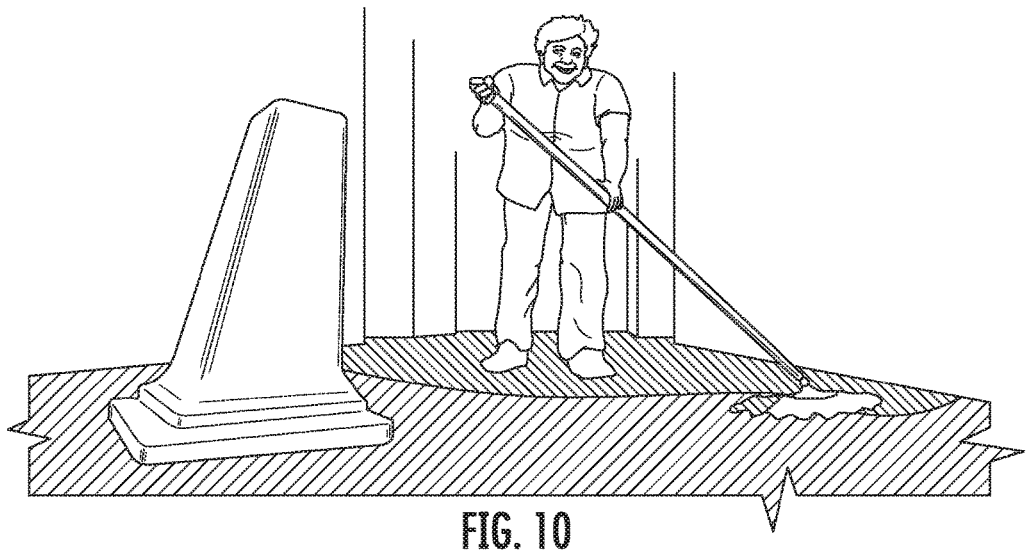
FIG. 10 is a perspective view of a worker cleaning a floor that may be captured by one or more video cameras.
Figure 11:
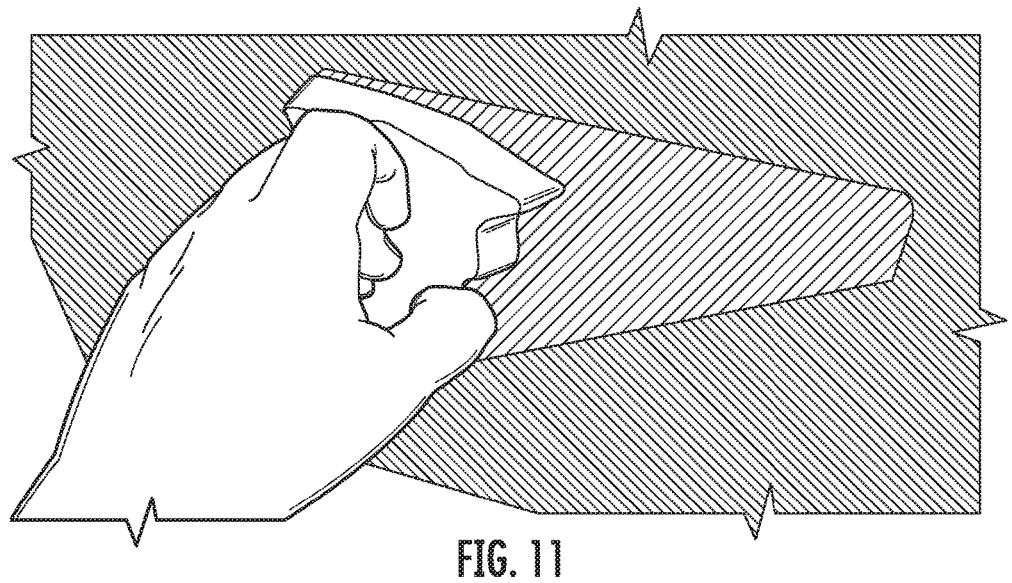
FIG. 11 is a perspective view of a sponge cleaning a surface that may be captured by one or more video cameras.

FIGS. 10 and 11 illustrate examples of using this light projection technique. In FIG. 10, the surface to be cleaned is the floor. Areas where the cleaner has mopped the floor (cleaned areas 42) have no specific light projected upon them, while areas still to be cleaned (unclean areas 44) have a special light projected upon them. The special light may be a specific color that is easily distinguishable from the background lighting such that the cleaner can distinguish it from the normal overhead lighting that illuminates the room, hallway, or other area. The determination of where to display this light on the surface being cleaned is based upon images taken from one or more cameras 22 and the analysis of those images to determine what areas have been cleaned. This processing and updating of the projected light takes place substantially in real time such that, as the cleaning personnel move their cleaning utensil over the surface, the projected light disappears in the area of the cleaning swath virtually immediately, or within seconds thereafter.

FIG. 11 illustrates a surface of an object being cleaned by a sponge 46. The cleaned areas 42 are not highlighted with specific light projected from projector 30. The uncleaned areas 44 are highlighted with the specific light from projector 30.

System 20 may also tracks what objects/areas have been touched and potentially contaminated since previous cleaning. A display associated with computer device 24 may show if any non-typical areas have been potentially contaminated.

Regardless of whether any light is projected during a cleaning process, system 20 may monitor the cleaning process by first identifying individuals who enter a given area who are janitors, or otherwise assigned to perform cleaning tasks. This recognition may be done by facial recognition, badge recognition, uniform recognition, combinations of these, or by other methods. Once a cleaning person is identified, system 20 may determine the location of a mop or other utensil held by the cleaning person. The end of the mop, or other cleaning utensil, that is used for cleaning may be recognized by comparing the detected data from cameras 22 with stored data corresponding to the mop or other cleaning instrument. As the individual performs his or her cleaning, those areas of the floor, or other surface being cleaning, are recorded by cameras 22. If the complete surface area of the floor, or other object, are not cleaned prior to the individual leaving the room, an alert may be issued.

D. Fall Prevention

System 20 may also be used to help prevent patient falls, as well as to detect when a patient fall occurs so that faster responses can be implemented, as well as to improve algorithms used to predict and prevent future falls.

1. Patient Behavior Recognition

Figure 12:
FIG. 12 is a perspective view of a patient about to exit a bed that may be captured by one or more video cameras.

In one embodiment, system 20 may monitor images from cameras 22 to predict behavior that leads to someone getting out of bed. This may include recognizing when a patient is awake, as opposed to sleep. This may further include recognizing the removal of sheets, or the movement external objects out of the way, such as, but not limited to, an over bed table (OBT), a phone, a nurse call device, etc.). This may also include recognizing when a patient swings his or her legs, grabs a side rail, inches toward a bed edge (such as shown in FIG. 12), lifts his or her torso, finds his or her slippers or other footwear, or other actions.

System 20 may also recognize when a patient is asleep and if the patient is sliding out of bed.

System 20 may further analyze images to predict behavior that leads to someone getting out of a chair or other piece of furniture. Such behavior may includes the removal of sheets, the movement of external objects out of the way (OBT, phone, nurse call, etc.), a patient leaning forward, grabbing chair arms, finding slippers, or the like.

The software within computer device 24 of system 20 may further be programmed to predict behavior that leads to a fall. Such predictions may be based upon analyzing images that show a patient's use of chair arms to get up, or patient bouncing, stooped posture, head down, short & shuffled steps, the grasping of nearby furniture/items, and other factors.

System 20 may also help to prevent falls by determining the location of the siderail on the patient's bed and whether the siderails are in the up or down position. This may be accomplished by storing in database 50 baseline information about the size and shape of the bed's siderails. The three dimensional coordinates of the bed and the side rails may be determined by the cameras 22 and the vertical components of the bed and siderails may be calculated to determine if the siderails are up or down. System 20 may also define regions close to the outer periphery of the bed as regions of higher risk. Patient movement toward these regions may trigger a pre-bed exit alert. A fall risk may also be detected based upon the locations of the patient's knees, hand, and feet when they are positioned within the higher risk area.

System 20 may further detect when a patient places his or her hands over a side rail. The coordinates of the patient's feet and other body extremities may be compared to each other and it may be determined whether any of these fall outside the bed outline coordinates. The center of gravity of the patient may be estimated and a higher likelihood of a patent exiting the bed may be concluded when the vertical component of the patient's center of gravity increase, or when the vertical component of the position of the patient's head increases. The detection of a patient leaning over a side rail can also increase an estimate of the likelihood of a patient leaving the bed. Movement of the patient toward a side rail, or toward the side of the bed closest to the bathroom, may also increase an estimate of the likelihood of the patient leaving the bed. The removal of sheets and the sitting up of a patient in bed may also increase this estimate. In any of the various embodiments, system 20 may be configured to calculate a likelihood of a patient making an imminent departure from the bed, based on any of the aforementioned factors. If this estimate exceeds a predefined threshold, then an alert may be transmitted to appropriate caregivers. A numeric value corresponding to this estimation of the likelihood of a patient exiting the bed may also be displayed on one or more screens that are viewable by a caregiver, including the screens of mobile devices, such as smart phones, laptops, tablet computers, etc.

The foregoing factors may also be used for estimating the likelihood of a patient exiting a chair. Those factors relating to siderails can be replaced with comparable factors relating to any armrests that are positioned on the chair. An assessment of the likelihood of the patient leaving the chair can also be displayed on one or more screens that are viewable by a caregiver, including the screens of mobile devices, such as smart phones, laptops, tablet computers, etc.

In addition to attempting to prevent a fall, system 20 may also detect a fall after it occurs. Such detection may occur by way of determining the proximity of a patient's head to the floor, sudden movement of the patient's head, arm movement to catch themselves, or other actions or events. System 20 may be programmed to record a fall event. In one embodiment, video images may be recorded over prior video images on a cyclical basis, such as every 24 hours unless an event happens. In such a case, the event, as well as a predetermined amount of time prior to the event (e.g. 30 minutes before it) may be saved to long-term memory for future analysis.

System 20 may also analyze fall events to make future algorithms more robust. Such analysis may also provide data to clinicians.

In any of the situations where it is desirable to monitor the patient's behavior, suitable algorithms may be used for monitoring the patient's location even when he or she is covered by bed sheets and/or blankets. Such algorithms may be activated when system 20 determines that a patient is positioned in bed and system 20 further determines that a sheet or blanket is being moved.

2. Clinician Behavior Recognition

In preventing falls, system 20 may further detect when a clinician enters a room. Such recognition may be done by facial recognition, badge identification, attire recognition, or other methods. When a clinician is in a room, system 20 may communicate information to the hospital bed, or a computer in communication with the hospital bed, that automatically pauses the bed's exit signaling system or the system's own fall prevention monitoring system while the clinician is in the room.

System 20 may also detect when a clinician approaches bed and system 20 may auto-retract a deployed floor mat to prevent tripping. System 20 may detect when a clinician leaves room the, such as by facial recognition, badge identification, attire recognition, or the like, and automatically terminate the pause in the bed's bed exit signaling system.

3. Monitoring Fall Protocols

System 20 may be further configured to check specified fall protocols when a clinician is not present in a room. Such protocols may involve checking the patient's bed height (whether it is low or not, as was described previously), whether the bed's brakes are set, whether the bed's side rails are up, whether the bed's bed exit signaling is set, and other bed features that are useful for reducing the likelihood of a patient fall. System 20 may communicate with the bed such that the brakes set automatically after a predetermined length of time after the bed is moved into the room (five seconds, for example, although other times may be used). In addition, system 20 may check that the bed, nurse call cable or other device is plugged in prior to the caregiver leaving the patient room. Such an event could trigger a local alarm initiated by system 20. System 20 may also use cameras 22 to monitor whether the bed, or another device, is plugged in or not plugged in. In the case of a bed, system 20 may warn the caregiver to unplug the bed or other device after its brakes are disengaged to prevent damage to the device or facility during movement of the device.

System 20 may further perform image and data analysis for doing patient checks, such as determining whether a patient has hip protectors, colored ID badges indicating increased fall risks, a helmet, anti-slip socks, or other characteristics that tend to indicate an increased risk of a fall.

System 20 may perform image analysis of the room in which the patient is positioned to assess obstacles that may lead to increased fall risks. Such room checks may includes checking to see if a floor mat in the right location, as well as checking for signs, obstacles, spills, a clear path to bathroom, and the like. Alternatively or in addition to a full-room scan, a user interface into system 20, which may include a keyboard, mouse, display, or other items, can allow a clinician to select what specific areas need to be clear of objects/obstacles for a particular patient. An example of such an area is the floor space between the bed and bathroom. System 20 can further identify objects in the room and determine whether a patient's needs are being met. Such patient needs may include determining whether various items are within physical reach of the patient. Such items may include a pillow, blanket, phone, OBT, drink, walker, or other objects which a patient is likely to have a desire for. If items that a patient may wish to reach for are not within reach of the patient, an alert may be issued so that a caregiver can move the objects closer to the patient, thereby reducing the likelihood that a patient may move out of the bed in order to retrieve such objects.

System 20 may detect spills by capturing a baseline image of a video frame from one or more of cameras 22 when no spill is present. After that, images may be captured at set intervals. These subsequently captured images may be converted to grayscale images and compared to the baseline grayscale images. If a spill is detected based upon this comparison, the contours of the spill may be detected and monitored. An alert may be issued to have the spill cleaned. Any detected spills may be assumed by system 20 to lie within the same plane as the floor of the room in which it is detected, unless the spill is detected on a particular non-floor object.

4. Objective Assessment

In attempting to reduce the risk of patient falls, the images and data captured by cameras 22 may further be used to perform gait assessments on patients. Such gait assessments may identify a patient's use of the arms of a chair to get up, or they may identify a patient bouncing, a stooped posture, a patient's head tilting down, short & shuffled steps, grasping nearby furniture/items, etc. Such information may be used as part of a Morse gait assessment, or other type of gait assessment. Analysis of the images may also include a get-up-and-go test in which it is determined whether a patient is able to rise in a single movement, push up in one attempt, or whether multiple attempts are made before success, or if the patient is unable to rise (Hendrichs II assessment). Images may also be analyzed to determine if a patient's IV or Heparin lock might impede the patient's mobility. System 20 may also perform object recognition and usage as part of the Morse assessment.

The gait assessment may also utilize comparisons of the locations of the patient's feet relative to the patient's trunk and/or other areas. For example, the horizontal coordinates of the patient's feet may be determined and compared to a downward vertical projection of the trunk. If the patient's feet are outside of this downward vertical projection, this may be an indicator of an unstable gait. Further, if the vertical coordinates of the patient's feet are above ground for more than minimal amounts of time, this also may indicate an unstable gait.

5. Remote Broadcasting

Whenever system 20 analyzes data from cameras 22 and determines an event, situation, or condition that warrants notification, system 20 may send appropriate message to a nurse's station. Alternatively, system 20 may send signals to one or more nurse's mobile device. In other embodiments, system 20 may send data to a private website for family member's computer access. Such a website might allow cameras 22 to be used for remote visiting or monitoring. In other words, one or more of the images from the cameras 22 could be forwarded to the website such that family members could see the patient from a remote location. Voice transmission capability could also be added so that voice communication between the patient and the remote family member could take place simultaneously with the transmission of live video.

The forwarding of patient data by system 20 to other systems and/or databases can be used for a wide variety of purposes, including remote monitoring which can include statistics of how often a nurse checked on patient, restlessness, medications, schedule, etc.

6. Alarming

If an event, condition, or situation detected by one or more video cameras 22 gives rise to a low risk status, system 20 may give out a warning. In the case of a high risk status, system 20 may give out alarms. Automatic voice signals may be transmitted to speakers within the patient's room. Such signals may include warning phrases, such as "do you need help?" or "a nurse has been called," or alarm phrases such as "get back in bed, Mr. Johnson" using the patient's name specifically or a beeping sound.

Such signals desirably can also provide context as to why an alarm is going off. For example, an alarm may state that "you are a fall risk, Mr. Johnson, because you are on medication and just had surgery."

Any alarms may be accompanied by a light to alert clinicians what room the alarm is in. Remote alarms to clinicians may also state the room number.

7. Other Sensors

In addition to video cameras 22, other sensors may be incorporated into system 20 for providing additional data that may be useful in carrying out any of the functions described herein. Such additional sensor may include radio frequency identification (RFID) tags, which may be attached to either personnel or objects, or both. Pressure or force transducers positioned within a bed, or in other locations, may also forward data to system 20 for use in the analyses discussed herein. Also, as was mentioned previously, cameras 22 may include the ability to take thermal images, either in addition to, or in lieu of, the visual images and depth data discussed herein. Such thermal imaging may be used to detect human beings behind obstructions, such as a patient lying under a bed sheet. Other depth sensors like sonar may also be used to identify the human contour under the bed sheet which a video image may not be able to capture.

8. Other Conditions

System 20 may also be used to detect multiple other conditions besides any of those previously mentioned. As one example, system 20 may be used for providing code pink alerts in nurseries, or other areas of a patient care facility where newborns are present. In such cases, cameras 22 may be positioned at areas outside of patient rooms. Specifically, cameras 22 may be placed at areas where they are able to detect any movement of a baby outside of a pre-designed acceptable area for the baby. That is, cameras 22 may be positioned so that they can detect any movement of a child that is not authorized without the permission of a caregiver, staff member, or other authorized employee, or any movement of a child outside of a predefined area that occurs in the presence of a non-parent or non-authorized employee. In such situations, system 20 may be configured to identify individuals through face recognition or other means. System 20 may further be configured to identify infants. The coordinates of the infant may be determined from the frames recorded by one or more cameras 22. The horizontal component or components of this position may then be compared with the predefined threshold areas. In one embodiment, if the child moves beyond these thresholds, an alert may be issued, regardless of what other adults may be accompanying the child. In another embodiment, if the child moves beyond a threshold, an alert may be issued only if the child is not accompanied by either its parent or an authorized employee of the hospital. In still other embodiments, a mixture of both types of alerting may be present for different thresholds within the hospital, or other type of patient care facility.

In other embodiments, computer device 24 and/or another computer in communication with system 20, may receive information from any one or more electronic devices or sensors that are positioned within the field of view of the cameras 22. System 20 may use this information in monitoring any of the conditions described herein, or in performing any of the algorithms described herein. Such information may also be used for other purposes. For example, in at least one embodiment, system 20 may be in communication with a sensor sheet positioned underneath the patient that detects the amount of pressure the patient is experiencing at substantially all portions of his or her body. System 20 may use this information to project patterns of colored light onto the patient's body while he or she is in bed. An example of this is shown in FIG. 17.

Figure 17:
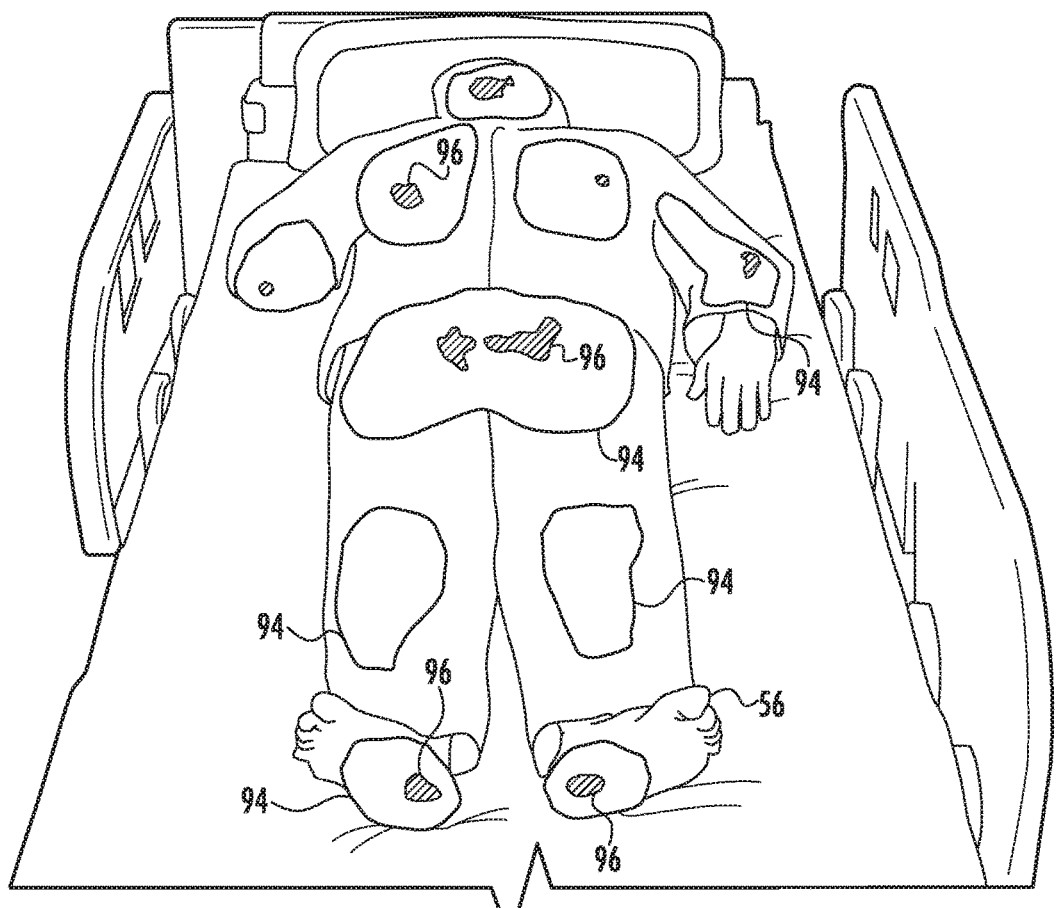
FIG. 17 is a perspective view of a patient wherein a color coded pressure map is projected onto the patient.

As shown in FIG. 17, there are different areas of the patient's body that are illuminated in different colors. The color of the light corresponds to the amount of pressure currently being experienced by that portion of the patient's body. For example, first areas 94 in FIG. 17 may be coded with a specific color and indicate mild amounts of pressure that the patient is currently experiencing. Second areas 96 may be coded with a different color and indicate higher amounts of pressure that are currently being experienced by the patient. Additional color coding may further be used to provide greater granularity of the pressure amounts being experienced. Regardless of the specific number of colors used, a clinician is provided with a colorized pressure map of the patient that is projected directly onto the patient's body. Those areas experiencing high pressure could then be moved by the caregiver to alleviate the pressure and/or change the location of the pressure, thereby reducing the likelihood of bed sores forming on the patient.

It will be understood by those skilled in the art that system 20 may be varied from the embodiments described above and that system 20 may be configured to monitor any one or more of the conditions described above.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A bed system for a patient care facility comprising:
a bed comprising a base, a plurality of wheels coupled to the base, a brake for braking the wheels, and a patient support surface supported on the base and configured to support a patient thereon;
a camera positioned within a room of the patient care facility and configured to capture images of a location within the room and output signals representative of the images;
a database containing shape information regarding a shape of the bed and identity information regarding identities of staff of the patient care facility; and
a computer device in communication with the camera, the database, and the bed, the computer device configured to use the signals and the shape information to determine when the bed is moved into the location, to use the signals and the identity information to identify a staff member accompanying the bed when the bed is moved into the location, to use the signals and the identity information to determine when the staff member departs from the room, and to automatically send a signal to the bed causing the bed to activate the brake on the bed if the staff member does not activate the brake.

2. The bed system of claim 1 wherein the computer device is further configured to generate a skeleton of the staff member.

3. The bed system of claim 2 wherein the camera includes a depth sensing device configured to detect a distance between the depth sensing device and objects positioned within a field of view of the camera, and the computer device is further configured to determine a three dimensional position of a plurality of points of the skeleton.

4. The bed system of claim 3 wherein the plurality of points of the skeleton correspond to at least two of the following locations of the staff member's body: a head, neck, shoulders, elbows, wrists, hands, trunk, hips, knees, ankles, and feet.

5. The bed system of claim 1 wherein the identity information includes information regarding a badge worn by the staff member.

6. The bed system of claim 1 wherein the database further includes nurse call cable information regarding a nurse call cable used with the bed, and wherein the computer device is further configured to use the nurse call cable information and signals to determine if the nurse call cable is plugged into a nurse call cable outlet.

7. The bed system of claim 6 wherein the computer device issues an alert if the nurse call cable is not plugged into a nurse call cable outlet prior to the staff member departing the room.

8. The bed system of claim 1 wherein the bed further comprises a bed exit signaling system in communication with the computer device, and wherein the computer device is further configured to send a pause signal to the bed causing the bed to pause the exit signaling device when the computer device detects the staff member in the room.

9. The bed system of claim 8 wherein the computer device is further configured to send a signal to the bed causing the bed to stop pausing the exit signaling device when the computer device detects the staff member departing the room.

10. The bed system of claim 1 wherein the computer device is a server coupled to a computer network of the patient care facility.

11. A bed system for a patient care facility comprising:
a bed comprising a base, a patient support surface supported on the base and configured to support a patient thereon, and an exit signaling device configured to issue an alert when a patient exits from the patient support surface;
a camera positioned within a room of the patient care facility and configured to capture images of a location within the room and output signals representative of the images;
a database containing identity information regarding identities of staff of the patient care facility; and
a computer device in communication with the camera, the database, and the bed, the computer device configured to use the signals and the identity information to identify a staff member when the staff member is positioned within the room, the computer device further configured to send a message to the bed causing the bed to pause the exit signaling device when the staff member is positioned within the room.

12. The bed system of claim 11 wherein the computer device is further configured to use the signals and identity information to determine when the staff member departs from the room and to send a message to the bed to stop the pause of the exit signaling device.

13. The bed system of claim 11 wherein the camera includes a depth sensing device configured to detect a distance between the depth sensing device and objects positioned within a field of view of the camera, and wherein the computer device is further configured to generate a skeleton of the staff member and to determine a three dimensional position of a plurality of points of the skeleton, the plurality of points corresponding to at least two of the following locations of the staff member's body: a head, neck, shoulders, elbows, wrists, hands, trunk, hips, knees, angles, and feet.

14. The bed system of claim 11 wherein the identity information includes information regarding a badge worn by the staff member.

15. The bed system of claim 11 wherein the identity information includes characteristics of the staff member's face.

16. The bed system of claim 11 wherein the identity information includes characteristics of the staff member's attire.

17. The bed system of claim 11 wherein the computer device is further configured to identify a location of the patient's head in the images, to automatically blur that location in the images, and to store the blurred head images without storing any unblurred images of the patient's head.

18. The bed system of claim 11 wherein the computer device is a server coupled to a computer network of the patient care facility.

19. The bed system of claim 11 wherein the camera is a thermal camera and the images are thermal images.

20. The bed system of claim 11 wherein the database include information about at least one of a shape, color, and size of the bed, and the computer device is further configured to determine from the signals a current angle of a head portion of a bed and initiate an alert to the staff member if the current angle of the head portion of the bed is less than a predetermined value.

* * * * *